(12) United States Patent
Tsai

(10) Patent No.: US 8,563,737 B2
(45) Date of Patent: Oct. 22, 2013

(54) METHODS OF MAKING BIS-TRIDENTATE CARBENE COMPLEXES OF RUTHENIUM AND OSMIUM

(75) Inventor: Jui-Yi Tsai, Newtown, PA (US)

(73) Assignee: Universal Display Corporation, Ewing, NJ (US)

( * ) Notice: Subject to any disclaimer, the term of this patent is extended or adjusted under 35 U.S.C. 154(b) by 304 days.

(21) Appl. No.: 13/033,160

(22) Filed: Feb. 23, 2011

(65) Prior Publication Data

US 2012/0215000 A1 Aug. 23, 2012

(51) Int. Cl.
*C07F 15/00* (2006.01)
*C07D 403/10* (2006.01)

(52) U.S. Cl.
USPC ............. 548/103; 548/305.1; 548/108; 546/4

(58) Field of Classification Search
USPC ............................ 548/103, 108, 305.1; 546/4
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0092854 A1 | 4/2009 | Walters et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |

FOREIGN PATENT DOCUMENTS

| | | |
|---|---|---|
| EP | 0650955 | 5/1995 |
| EP | 1725079 | 11/2006 |
| EP | 2034538 | 3/2009 |
| JP | 200511610 | 1/2005 |
| JP | 2007123392 | 5/2007 |
| JP | 2007254297 | 10/2007 |
| JP | 2008074939 | 10/2009 |
| WO | WO 0139234 | 5/2001 |
| WO | WO 0202714 | 1/2002 |
| WO | WO 0215645 | 2/2002 |

(Continued)

OTHER PUBLICATIONS

Baldo et al., "Highly Efficient Phosphorescent Emission from Organic Electroluminescent Devices," Nature, vol. 395, 151-154, (1998).

(Continued)

*Primary Examiner* — Charanjit Aulakh
(74) *Attorney, Agent, or Firm* — Duane Morris LLP

(57) ABSTRACT

Methods of making bis-tridentate carbene complexes of ruthenium and osmium are provided. The use of DMSO solvates of ruthenium(II) and osmium(II) halide salts provides good yields of the corresponding complexes. These materials may be used in OLEDs to provide devices having improved performance.

16 Claims, 3 Drawing Sheets

(56) References Cited

FOREIGN PATENT DOCUMENTS

| WO | WO 03040257 | 5/2003 |
|---|---|---|
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009/046266 | 4/2009 |
| WO | WO 2009050290 | 4/2009 |
| WO | WO 2009021126 | 5/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |

OTHER PUBLICATIONS

Baldo et al., "Very high-efficiency green organic light-emitting devices based on electrophosphorescence," Appl. Phys. Lett., vol. 75, No. 3, 4-6 (1999).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater, 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

Huang, Jinsong et al, "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int. Ed., 45:7800-7803 (2006).

Tang, C.W. and VanSlyke, S.A., "Organic Electroluminescent Diodes," Appl. Phys. Lett., 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(I) Complex-Based Light-Emitting Diodes with Low Turn-On voltage," Appl. Phys. Lett., 74(100:1361-1363 (1999).

Gao, Zhiqiang et al., "Bright-Blue Electroluminescence From a Silyl-Substituted ter-(phenylene-vinylene) derivative," Appl. Phys. Lett., 74(6):865- 867 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Hung, L.S. et al., "Anode Modification in Organic Light-Emitting Diodes by Low-Frequency Plasma Polymerization of $CHF_3$," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Wang, Y. et al., "Highly Efficient Electroluminescent Materials Based on Fluorinated Organometallic Iridium Compounds," Appl. Phys. Lett. 79(4):449-451 (2001).

Kwong, Raymond C. et al., "High Operational Stability of Electrophosphorescent Devices," Appl. Phys. Lett., 81(1):162-164 (2002).

Holmes, R.J. et al., "Blue Organic Electrophosphorescence Using Exothermic Host-Guest Energy Transfer," Appl. Phys. Lett., 82(15):2422-2424 (2003).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Okumoto, Kenji et al., "Green Fluorescent Organic Light-Emitting Device with External Quantum Efficiency of Nearly 10%," Appl. Phys. Lett., 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Aonuma, Masaki et al., "Material Design of Hole Transport Materials Capable of Thick-Film Formation in Organic Light Emitting Diodes," Appl. Phys. Lett., 90:183503-1-183503-3 (2007).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

Adachi, Chihaya et al., "High-Efficiency Red Electrophosphorescence Devices," Appl. Phys. Lett., 78(11):1622-1624 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Hamada, Yuji et al., "High Luminance in Organic Electroluminescent Devices with Bis(10-hydroxybenzo[h]quinolinato)beryllium as an Emitter," Chem. Lett., 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4):592-593 (2005).

Mi, Bao-Xiu et al., "Thermally Stable Hole-Transporting Material for Organic Light-Emitting Diode: an Isoindole Derivative," Chem. Mater., 15(16):3148-3151 (2003).

Huang, Wei-Sheng et al., "Highly Phosphorescent Bis-Cyclometalated Iridium Complexes Containing Benzoimidazole-Based Ligands," Chem. Mater., 16(12):24130-2488 (2004).

Niu, Yu-Hua et al., "Highly Efficient Electrophosphorescent Devices with Saturated Red Emission from a Neutral Osmium Complex," Chem. Mater., 17(13):3532-3536 (2005).

Lo, Shih-Chun et al., "Blue Phosphorescence from indium(III) Complexes at Room Temperature," Chem. Mater., 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," Inorg. Chem., 46(10):4308-4319 (2007).

Lamansky, Sergey et al., "Synthesis and Characterization of Phosphorescent Cyclometalated Iridium Complexes," Inorg. Chem., 40(7):1704-1711 (2001).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

(56) References Cited

OTHER PUBLICATIONS

Noda, Tetsuya and Shirota, Yasuhiko, "5,5'-Bis(dimesitylboryl)-2,2'-bithlophene and 5,5"- Bis(dimesitylboryl)-2,2':5∝,2"-terthiophene as a Novel Family of Electron-Transporting Amorphous Molecular Materials," *J. Am, Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials." *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergard et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_9$ Hole-Transport Molecules Based on Indolo[3,2-*b*] carbazoles for Organic Light-Emitting Devices," Synthetic Metals, 111-112:421-424 (2000).

Salbeck, J. et al., "Low Molecular Oganic Glasses for Blue Electroluminescence," *Synthetic Metals*, 91:209-215 (1997).

The International Search Report issued in PCT/US2012/026403, mailed Dec. 5, 2012.

Baker et al., "A new binding geometry for an ortho-xylylene-linked bis(NHC)cyclophane: a ruthenium(II) complex with a chelating ([eta]1-NHC)2: [eta]6-arene ligand", Dalton Transactions, vo 1 . 39, No. 1, Jan. 1, 2010 , p. 70.

Formula II

METHODS OF MAKING BIS-TRIDENTATE CARBENE COMPLEXES OF RUTHENIUM AND OSMIUM

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to methods of making carbene complexes, and more specifically, to methods of making bis-tridentate complexes of ruthenium and osmium.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

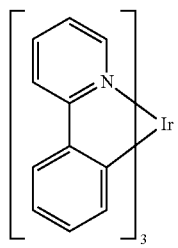

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A method of making a metal complex having the formula I is provided.

$$Q_1-M-Q_2 \qquad \text{Formula I}$$

The method comprises mixing a salt of formula $MX_2L_n$ with precursors of carbenes $Q_1$ and $Q_2$, wherein $Q_1$ and $Q_2$ are independently selected from a compound of formula II,

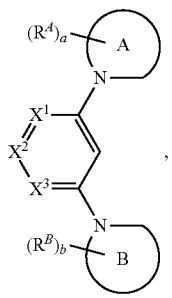

Formula II a carbene forming agent, solvent, and heating the reaction mixture. $Q_1$ and $Q_2$ can be the same or different.

In the metal salt $MX_2L_n$, M is a second or third row transition metal in the +2 oxidation state, X is a halogen, L is a ligand coordinated to M selected from the group consisting of DMSO, THF, and $CH_3CN$, and n is 2 to 4.

Rings A and B are independently selected from the group consisting of: (a) a 5-membered heterocyclic group, (b) an 8- to 12-membered bicyclic group having from 0 to 6 ring heteroatoms, (c) an 11- to 18-membered tricyclic group having from 0 to 7 ring heteroatoms, (d) an 11- to 14-membered fused tricyclic group having from 0 to 6 ring heteroatoms, and (e) an 14- to 18-membered fused tetracyclic group having from 0 to 7 ring heteroatoms. Ring A and/or ring B may form a salt, a is 0 to 4, and b is 0 to 4.

$X^1$ is selected from $C-R^1$ and N, $X^2$ is selected from $C-R^2$ and N, and $X^3$ is selected from $C-R^3$ and N.

In one aspect, $R^1$ and $R^2$, or $R^2$ and $R^3$ are linked to form a 5- or 6-membered cyclic group, an 8- to 10-membered fused bicyclic group, an 11- to 14-membered fused tricyclic group, which may be optionally substituted with one or more substituents independently selected from hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

In one aspect, $R^1$ and an $R^A$ are linked to form a 5- or 6-membered cyclic group, or an 8- to 10-membered fused bicyclic group.

In one aspect, $R^3$ and an $R^B$ are linked to form a 5- or 6-membered cyclic group, or an 8- to 10-membered fused bicyclic group.

The groups $R^A$, $R^B$, $R^1$, $R^2$, $R^3$, and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, M is ruthenium or osmium.

In one aspect, the carbene forming agent is selected from silver(I) oxide and copper(I) alkoxide. In one aspect, the copper(I) alkoxide is copper(I) tert-butoxide.

In one aspect, the metal salt has the formula $RuX_2(DMSO)_4$. In one aspect, the metal salt has the formula $RuCl_2(DMSO)_4$.

In one aspect, the metal salt has the formula $OsX_2(DMSO)_4$. In one aspect, the metal salt has the formula $RuCl_2(DMSO)_4$, In one aspect, the solvent comprises a polar solvent. In one aspect, the polar solvent comprises an alcohol. In one aspect, the alcohol is selected from the group consisting of 2-methoxyethanol, 2-ethoxyethanol, and mixtures thereof.

In one aspect, the precursors of carbenes $Q_1$ and $Q_2$ are independently selected from a compound of formula III:

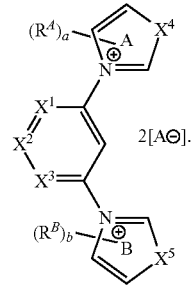

Formula III

In the compound of formula III, the dashed line represents an optional bond, $X^4$ is selected from N—R', O, and S, $X^5$ is selected from N—R', O, and S, and A is a counterion.

Specific, non-limiting examples of carbene precursors are provided. In one aspect, the carbene precursors are selected from the group consisting of Compound 1-Compound 75.

Also provided are ruthenium carbene complexes selected from the group consisting of Compound 76-Compound 82.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
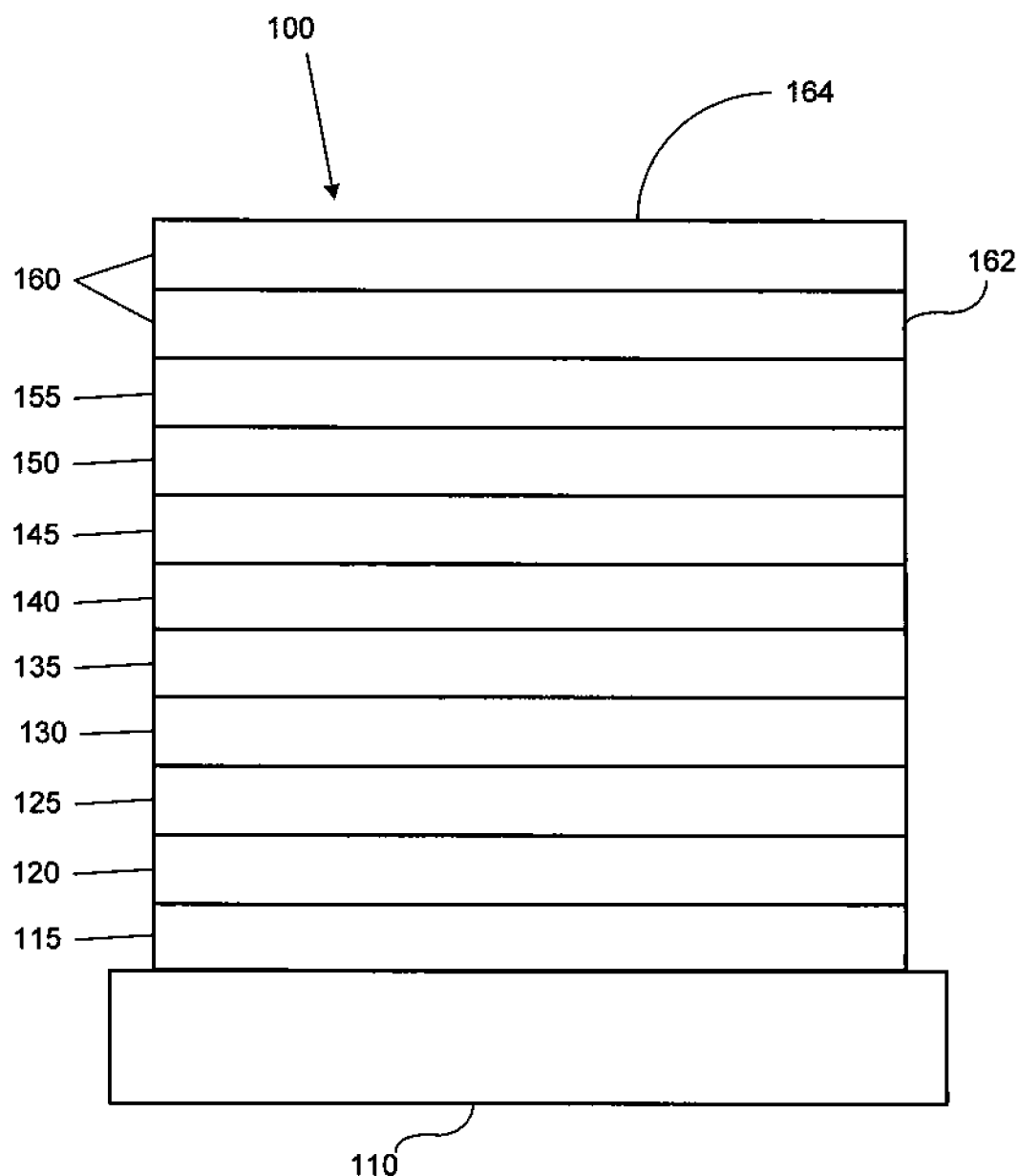
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
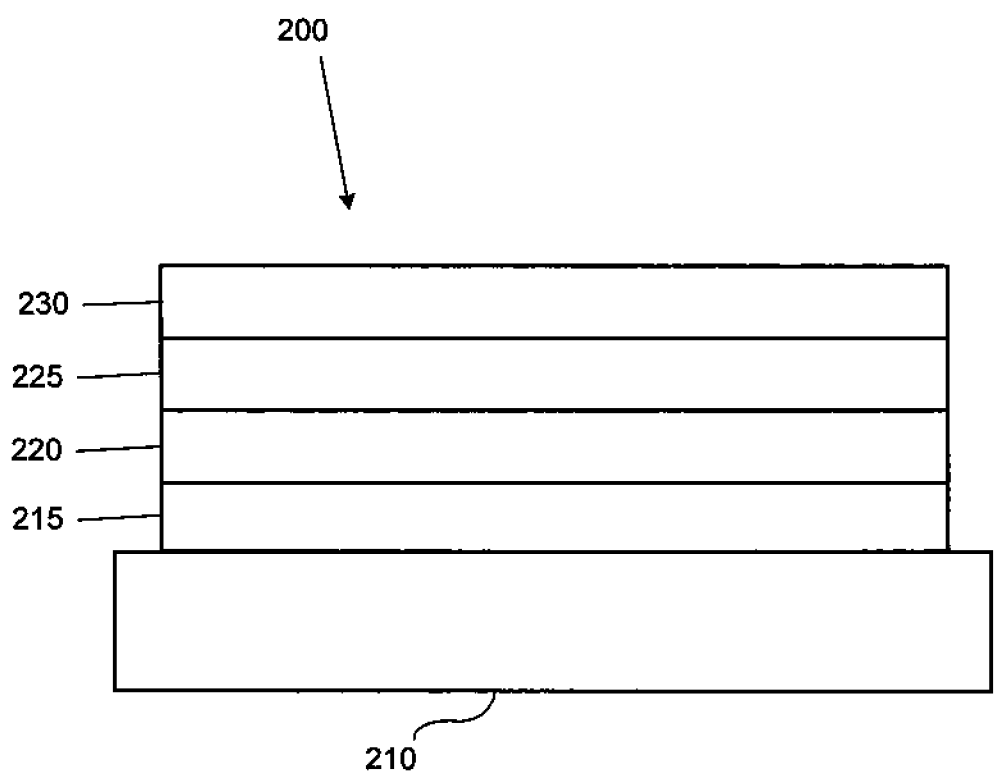
FIG. 2 shows an inverted organic light emitting device that does not have a separate electron transport layer.
Figure 3:
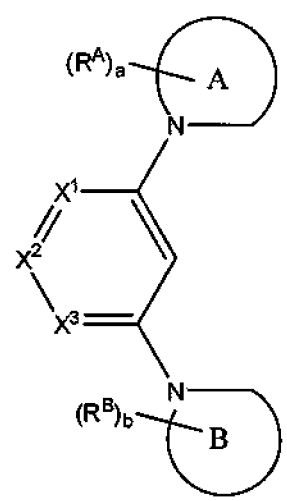
FIG. 3 shows the general structure of the carbene precursors that can be reacted with osmium and ruthenium according to the provided method.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Bis-tridentate carbene complexes of osmium and ruthenium complexes have unique properties in OLED applications, including extremely narrow line widths and short excited state lifetimes. However, the synthesis of these types of compounds has been problematic due to the low yield in the final step of complex formation, i.e. formation of the osmium or ruthenium carbene complex. Therefore, because of the desirability of these compounds for OLED applications, and the need for higher yields, a new method was needed to prepare compounds of formula I.

In a previous patent publication, WO2009046266, incorporated herein by reference, only a low 2-5% yield was obtained for the synthesis of a bis-tridentate osmium carbene complex. One of the challenges in synthesizing bis-tridentate carbene complexes of ruthenium and osmium in good yield is believed to stem from the difficulty in simultaneously activating the central aryl C—H bond along with the two N-heterocyclic carbene (NHC) C—H bonds in a single ligand. Since two deprotonations and a concurrent C—H activation are required, there have been limited examples of these complexes in the literature.

This difficulty has now been overcome by using a novel synthetic method to obtain the corresponding bis-tridentate carbene complexes in good yields. Table 1 illustrates various osmium metal salts used in the synthesis of bis-tridentate-osmium carbene complexes and using compound 35 and compound 75 as the carbene precursor. In one embodiment, the osmium or ruthenium halides in the +2 oxidation state are complexed with DMSO (dimethylsulfoxide), e.g. $OsCl_2(DMSO)_4$, $RuCl_2(DMSO)_4$.

Without being bound by theory, it is believed that the relative lability of the DMSO ligands allows for their facile displacement, and the subsequent complexation of the metal center with the carbene ligands provides the corresponding bis-tridentate osmium or ruthenium carbene complexes in good yield. For example, the reaction of $OsCl_2(DMSO)_4$ with silver oxide, and compound 35 as carbene precursor in 2-ethoxyethanol provided the corresponding osmium complex in 34% yield. An analogous reaction using $RuCl_2(DMSO)_4$ and compound 33 as the carbene precursor provided the corresponding ruthenium complex in 46% yield. Thus, other solvates of osmium(II) and ruthenium(II) halides are expected to be useful. In one embodiment, THF (tetrahydrofuran) and $CH_3CN$ solvates of osmium(II) and ruthenium (II) halides can be used. In comparison to $OsCl_2(DMSO)_4$, the other osmium complexes resulted in significantly lower yields.

TABLE 1

Effect of Metal Precursor on Yield of Bis-tridentate Carbene Complexes Using Compounds 35 and 75 as Carbene Precursor

| Deprotonation Agent of NHC C—H bond | Os Precursor | Ligation Yield (%) | Method in Experimental Section |
|---|---|---|---|
| $Ag_2O$ | $OsCl_2(DMSO)_4$ | 34 | A |
| $Ag_2O$ | $OsCl_2(PPh_3)_3$ | 4 | B |
| $K_2CO_3$ | $OsH_6((i-Pr)_3)_2$ | 12 | C |
| $Ag_2O$ | $[OsCl_2(benzene)]_2$ | 4 | D |
| $Ag_2O$ | $Os_3(CO)_{12}$ | No product detected | |

NHC derivatives that contain benzothiazole (i.e. N,S carbenes) and benzoxazole (i.e. N,O carbenes) functionality tend to be less stable than the corresponding imidazole or benzimidazole (i.e. N,N carbene) derivatives. Unlike N-substituted N,N carbenes, the carbene center in N,S and N,O carbenes is less sterically protected because the oxygen or sulfur atoms in these carbene derivatives cannot be substituted with, for example, an alkyl or aryl group. It was observed that synthesis of N,S and N,O containing carbene precursors did not proceed using silver oxide, and another method had to be developed. It was surprisingly discovered that a combination of copper(I) chloride and an alkali metal alkoxide as the carbene forming agent, instead of silver(I) oxide, allowed for the synthesis of N,S and N,O containing carbene complexes of osmium and ruthenium. Without being bound by theory, it is believed that a mixture of copper(I) chloride and an alkali metal alkoxide generates a reactive copper(I) alkoxide species. In one embodiment, the carbene forming agent is copper(I) alkoxide. In one embodiment the carbene forming agent is copper(I) tert-butoxide. In one embodiment, the method comprises using copper(I) chloride an alkali metal tert-butoxide as carbene forming agent, a N,S or N,O carbene precursor, and a suitable osmium or ruthenium metal salt to provide the N,S or N,O bis-tridentate carbene complexes described herein. The use of copper(I) chloride an alkali metal alkoxide is believed to be novel.

Accordingly, a method of making a metal complex having the formula I is provided.

$Q_1$-M-$Q_2$     Formula I

The method comprises mixing a salt of formula $MX_2L_n$ with precursors of carbenes $Q_1$ and $Q_2$, wherein $Q_1$ and $Q_2$ selected from a compound of formula II, which may be the same or different Formula II

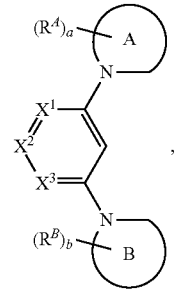

a carbene forming agent, solvent, and heating the reaction mixture. Compounds of formula I are believed to be useful materials in OLED applications.

In the metal salt $MX_2L_n$, M is a second or third row transition metal in the +2 oxidation state, X is a halogen, L is a ligand coordinated to M selected from the group consisting of DMSO, THF, and $CH_3CN$, and n is 2 to 4. In one embodiment, M is ruthenium or osmium.

In one embodiment, the carbene forming agent is selected from silver oxide and copper(I) chloride. In one embodiment, the metal salt has the formula $RuX_2(DMSO)_4$. In one embodiment, the metal salt has the formula $RuCl_2(DMSO)_4$. In one embodiment, the metal salt has the formula $OsX_2(DMSO)_4$. In one embodiment, the metal salt has the formula $RuCl_2(DMSO)_4$.

In one embodiment, the solvent comprises a polar solvent. In one embodiment, the polar solvent comprises an alcohol. In one embodiment, the alcohol is selected from the group consisting of 2-methoxyethanol, 2-ethoxyethanol, and mixtures thereof. Polar solvents such as alcohols are desirable due to their capacity to effectively solvate polar species such as carbene precursors $Q_1$ and $Q_2$.

Rings A and B are independently selected from the group consisting of (a) a 5-membered heterocyclic group, (b) an 8- to 12-membered bicyclic group having from 0 to 6 ring heteroatoms, (c) an 11- to 18-membered tricyclic group having from 0 to 7 ring heteroatoms, (d) an 11- to 14-membered fused tricyclic group having from 0 to 6 ring heteroatoms, and (e) an 14- to 18-membered fused tetracyclic group having from 0 to 7 ring heteroatoms. Ring A and/or ring B may form a salt, a is 0 to 4, and b is 0 to 4.

$X^1$ is selected from $C—R^1$ and N, $X^2$ is selected from $C—R^2$ and N, and $X^3$ is selected from $C—R^3$ and N.

In one aspect, $R^1$ and $R^2$, or $R^2$ and $R^3$ are linked to form a 5- or 6-membered cyclic group, an 8- to 10-membered fused bicyclic group, an 11- to 14-membered fused tricyclic group, which may be optionally substituted with one or more substituents independently selected from hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof;

In one aspect, $R^1$ and an $R^A$ are linked to form a 5- or 6-membered cyclic group, or an 8- to 10-membered fused bicyclic group.

In one aspect, $R^3$ and an $R^B$ are linked to form a 5- or 6-membered cyclic group, or an 8- to 10-membered fused bicyclic group.

The groups $R^A$, $R^B$, $R^1$, $R^2$, $R^3$, and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof.

In one aspect, the precursors of carbenes $Q_1$ and $Q_2$ are independently selected from a compound of formula III:

Formula III

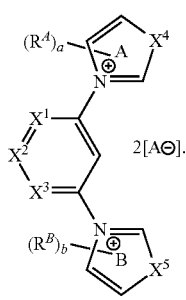

In the compound of formula III, the dashed line represents an optional bond, $X^4$ is selected from N—R', O, and S, $X^5$ is selected from N—R', O, and S, and A is a counterion.

Specific, non-limiting examples of carbene precursors are provided. In one aspect, the carbene precursors are selected from the group consisting of Compound 1-Compound 74.

In one embodiment, the precursors of carbenes $Q_1$ and $Q_2$ are independently selected from the group consisting of:

Compound 1

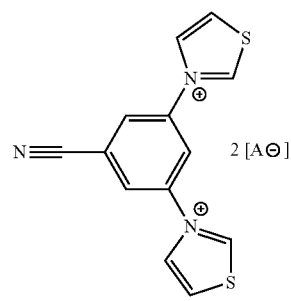

Compound 2

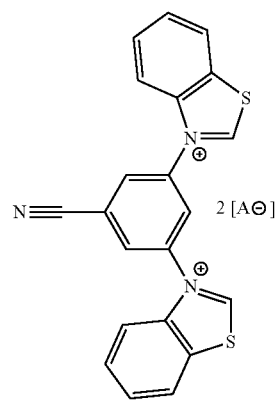

Compound 3

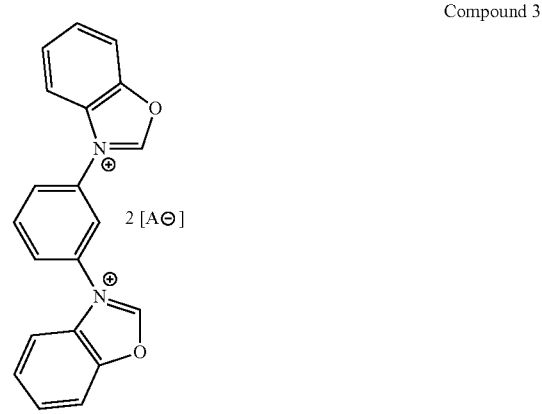

Compound 4

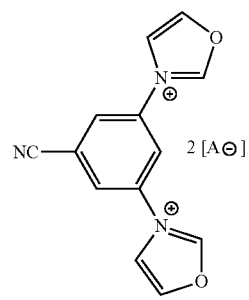

Compound 5
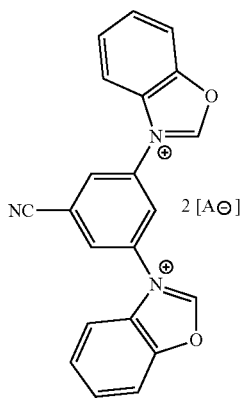
Compound 6
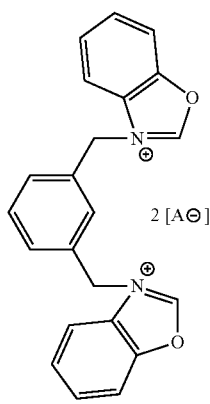
Compound 7
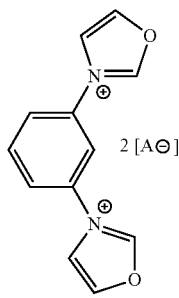
Compound 8
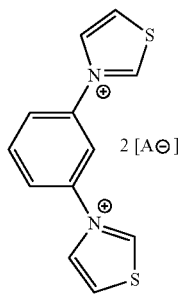
Compound 9
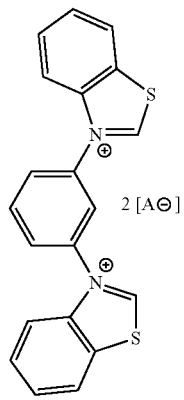
Compound 10
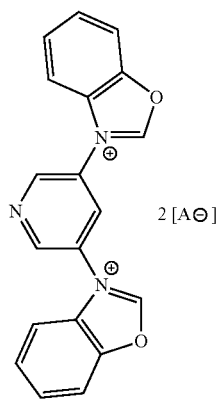
Compound 11
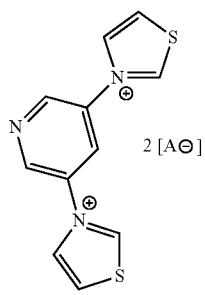
Compound 12
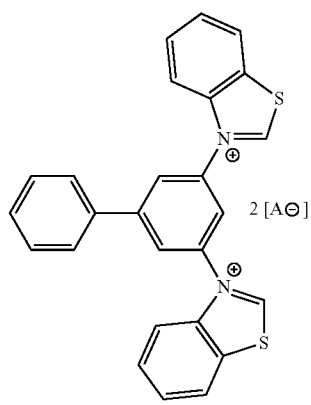

Compound 13
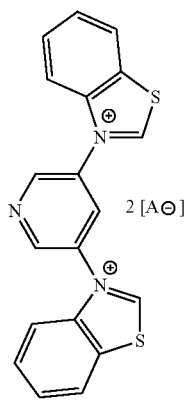
2 [A⊖]
Compound 14
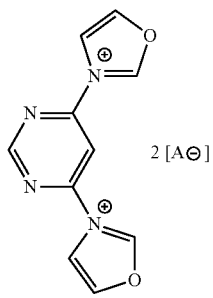
2 [A⊖]
Compound 15
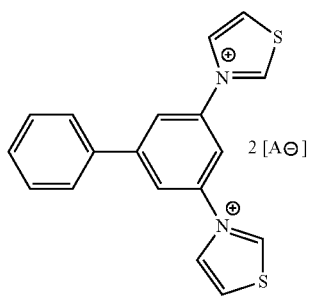
2 [A⊖]
Compound 16
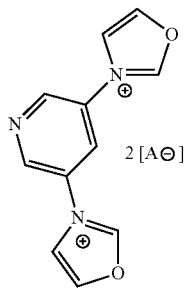
2 [A⊖]
Compound 17
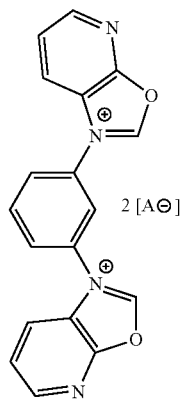
2 [A⊖]
Compound 18
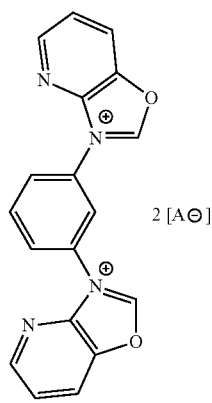
2 [A⊖]
Compound 19
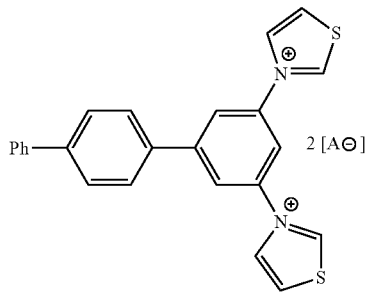
2 [A⊖]
Compound 20
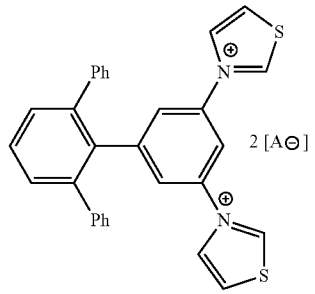
2 [A⊖]

-continued
Compound 21
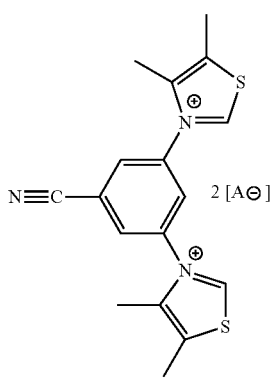
2 [A⊖]
Compound 22
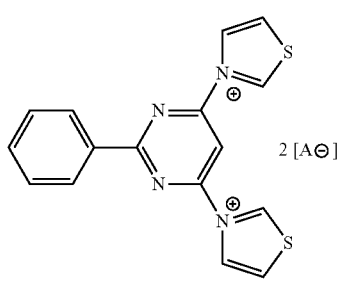
2 [A⊖]
Compound 23
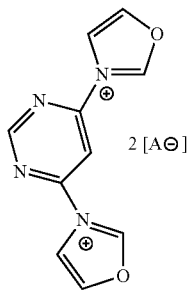
2 [A⊖]
Compound 24
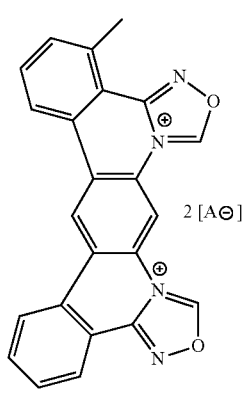
2 [A⊖]
-continued
Compound 25
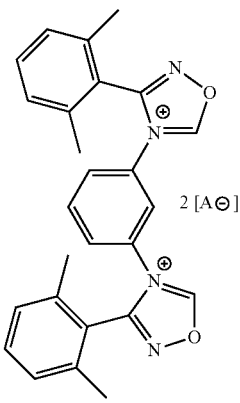
2 [A⊖]
Compound 26
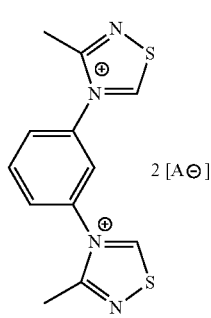
2 [A⊖]
Compound 27
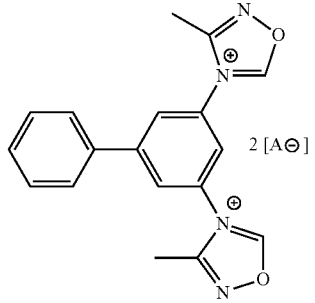
2 [A⊖]
Compound 28
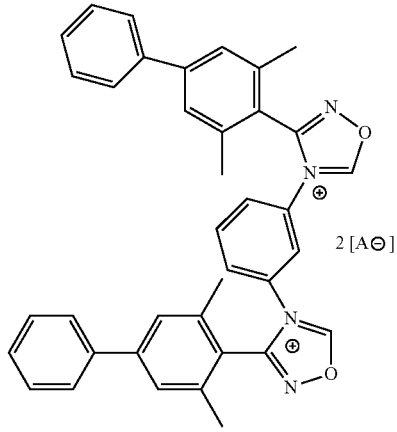
2 [A⊖]

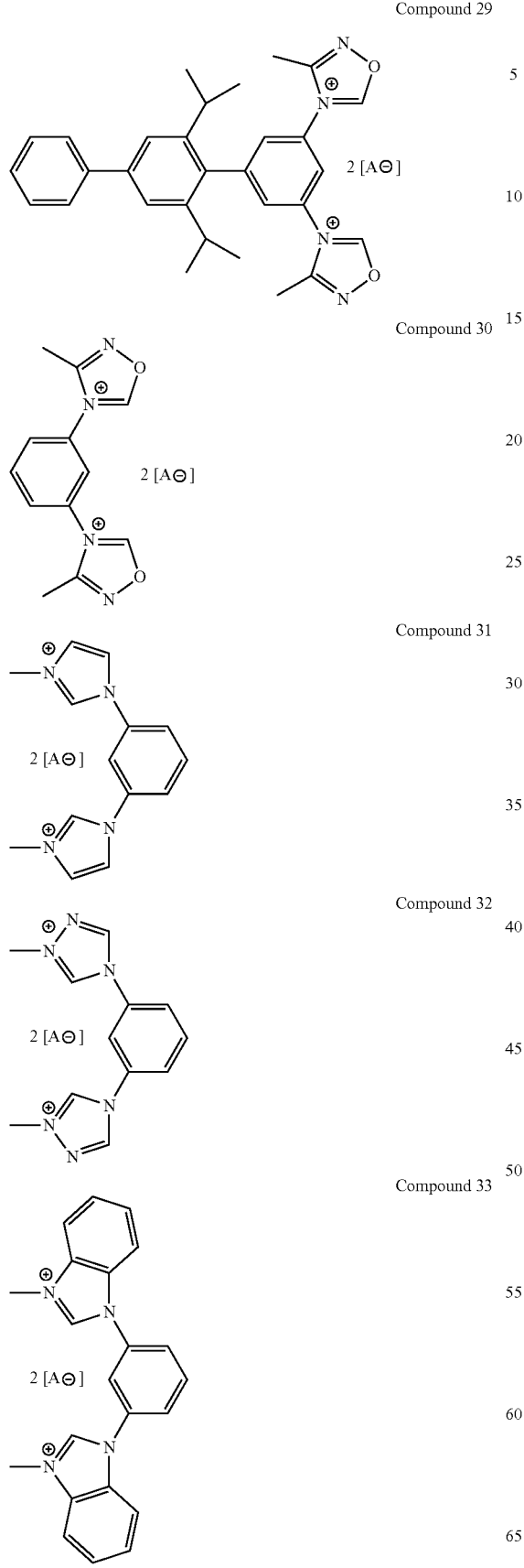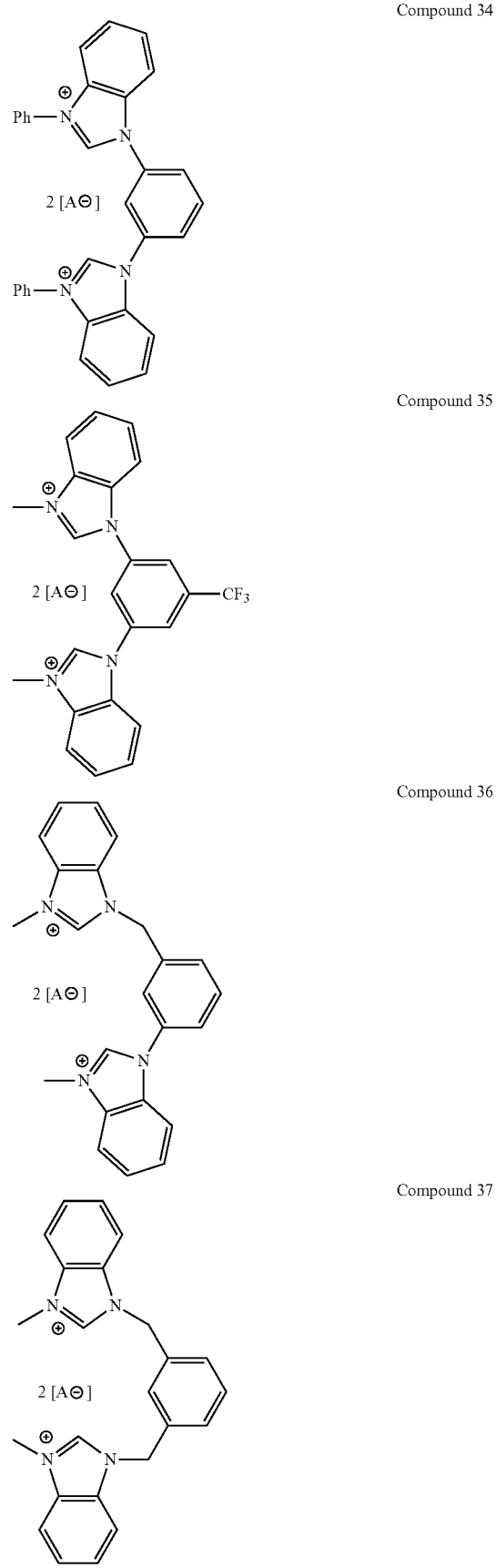

Compound 38
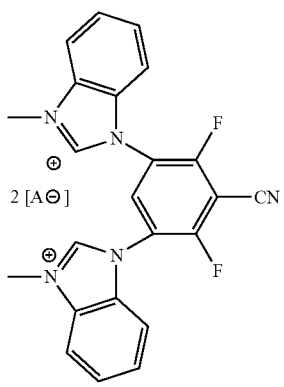
Compound 39
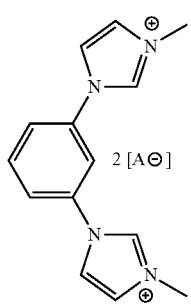
Compound 40
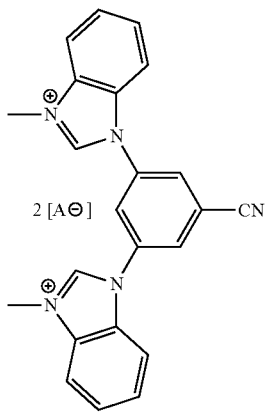
Compound 41
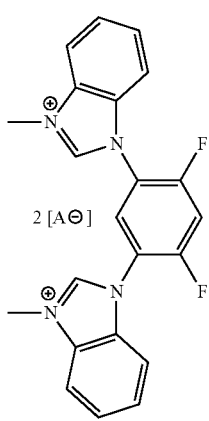
Compound 42
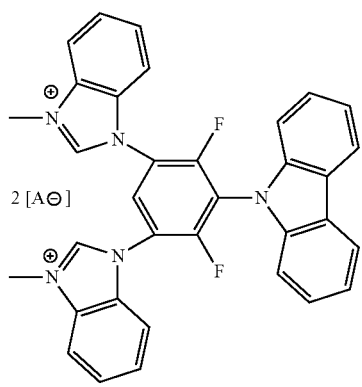
Compound 43
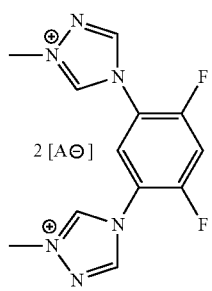
Compound 44
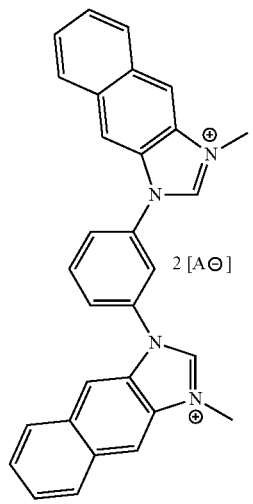
Compound 45
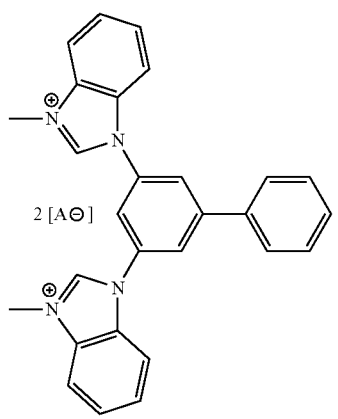

Compound 46
Compound 47
Compound 48
Compound 49
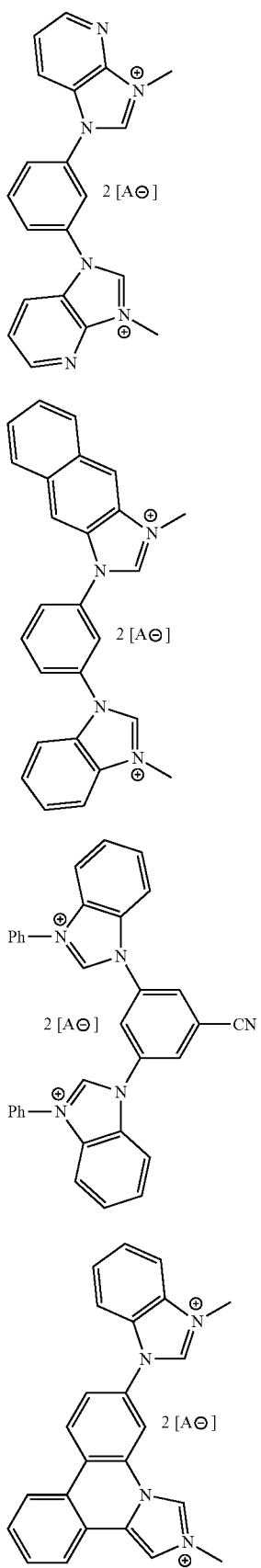
Compound 50
Compound 51
Compound 52
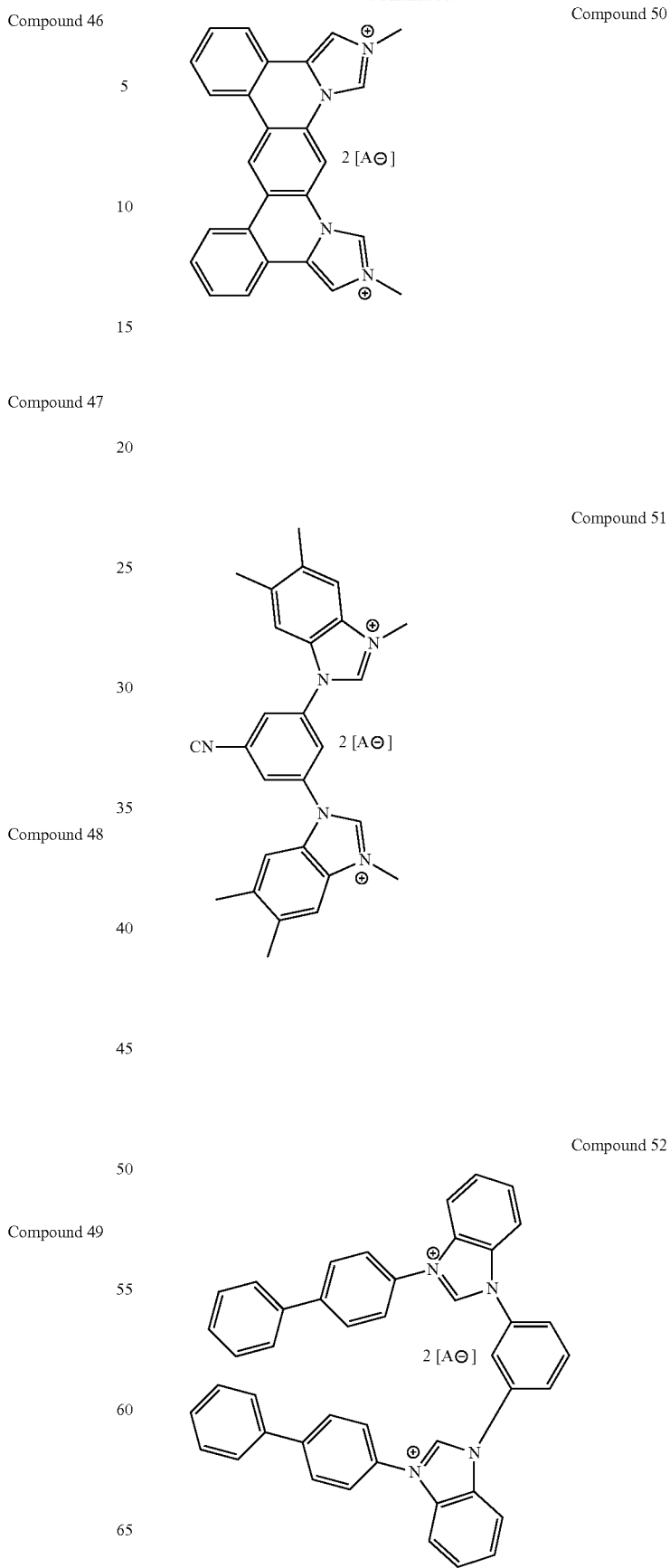

Compound 53

Compound 54

Compound 55

Compound 56

Compound 57

Compound 58

Compound 59

Compound 60

-continued
Compound 61
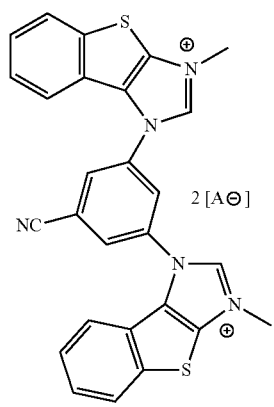
Compound 62
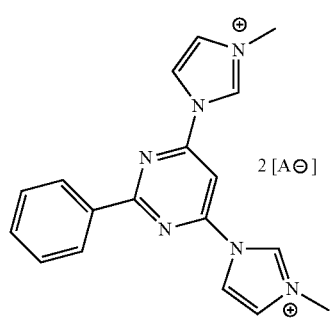
Compound 63
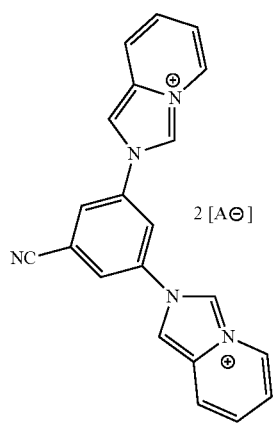
Compound 64
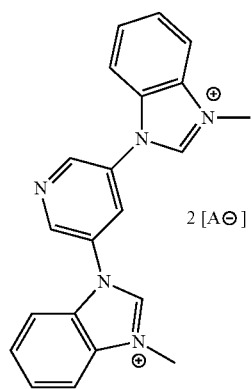
-continued
Compound 65
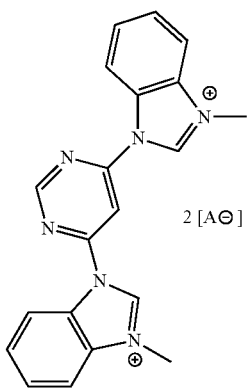
Compound 66
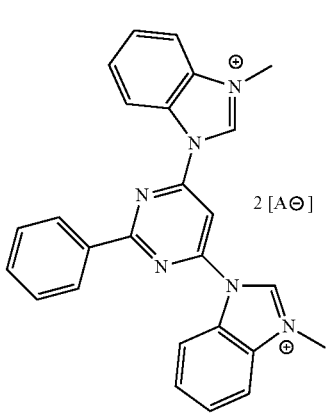
Compound 67
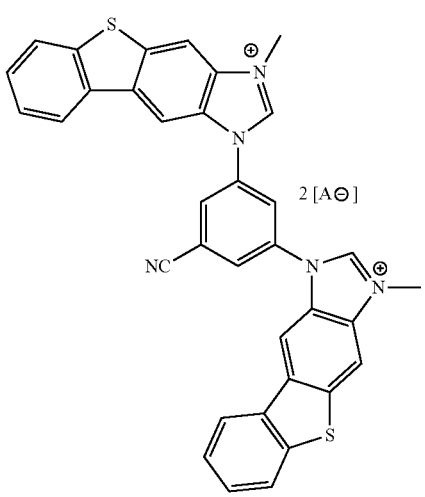

Compound 68
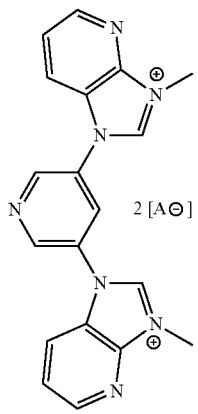
Compound 69
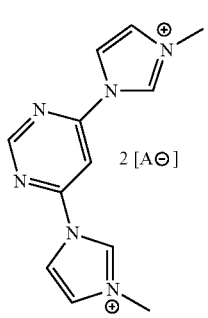
Compound 70
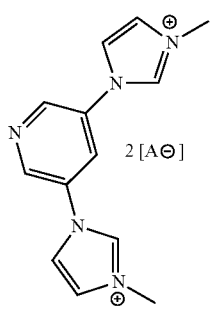
Compound 71
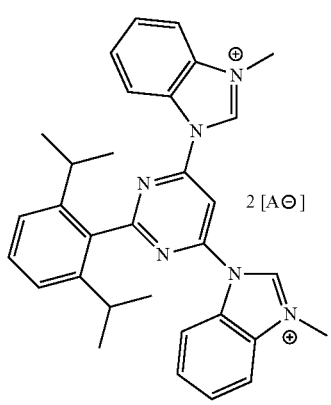
Compound 72
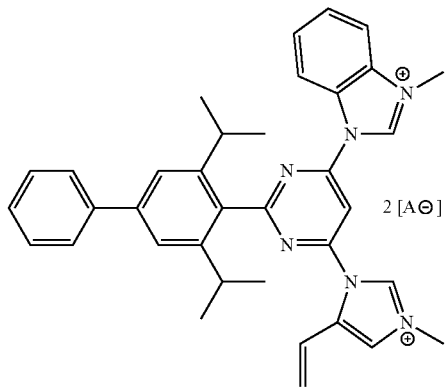
Compound 73
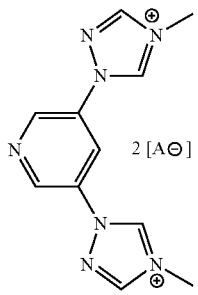
Compound 74
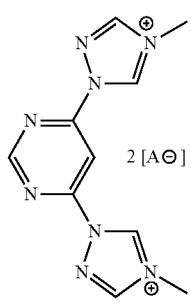
Compound 75
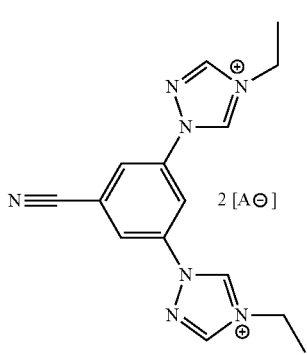
Also provided are ruthenium carbene complexes selected from the group consisting of:

Compound 76
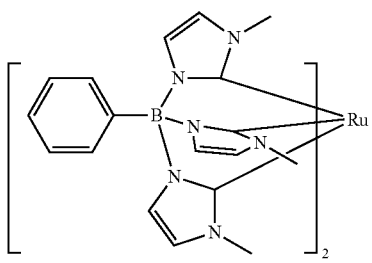

Compound 80
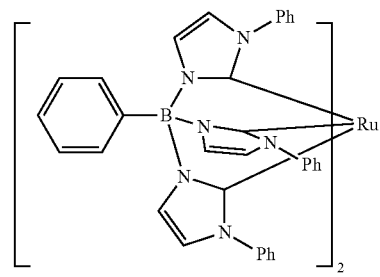

Compound 81
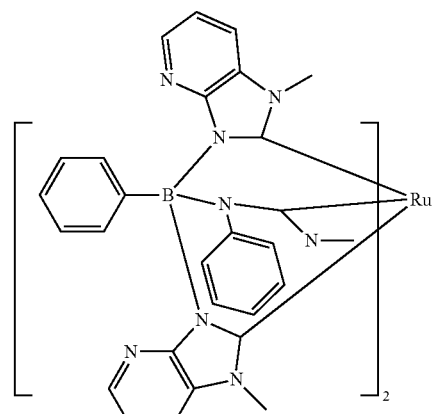

Compound 77
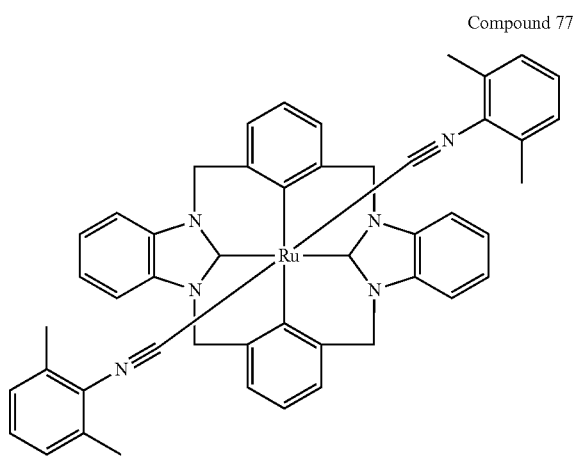

Compound 82
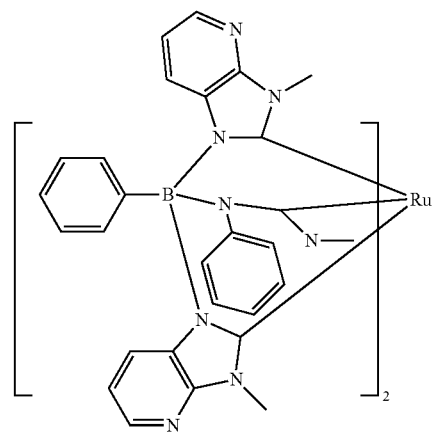

Compound 78
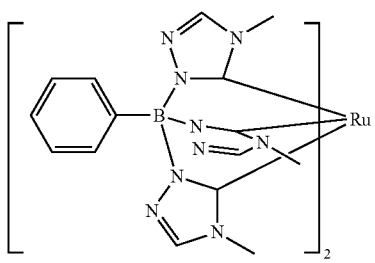

Compound 79
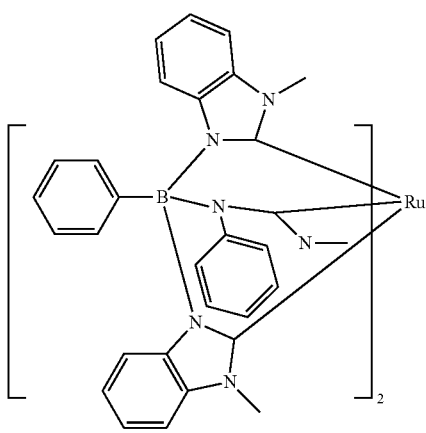

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in some embodiments of the present invention is not particularly limited, and any compound may be used as long as the compound is typically used as a hole injecting/transporting material.

Examples of the material may include, but are not limited to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL may include, but are not limited to, the following general structures:

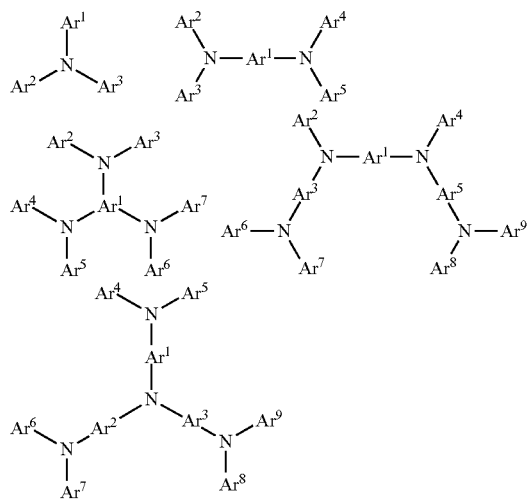

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxadiazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

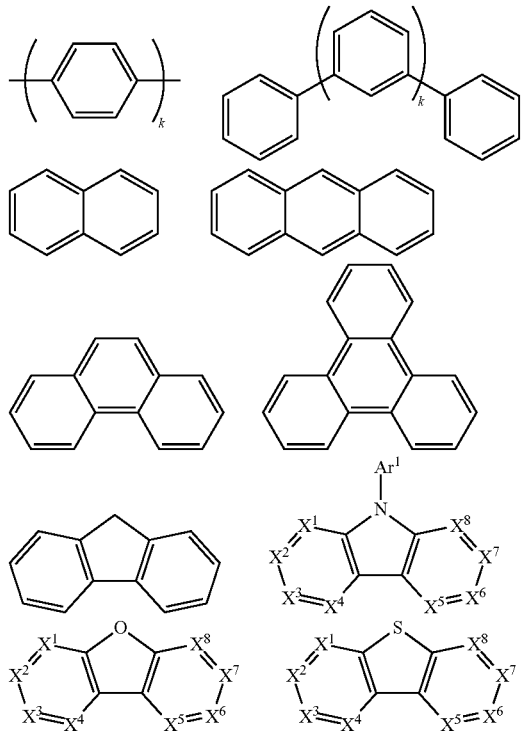

k is an integer from 1 to 20; $X^1$ to $X^8$ is CH or N; $Ar^1$ has the same group defined above.

Examples of metal complexes that may used in HIL or HTL include, but are not limited to, the following general formula:

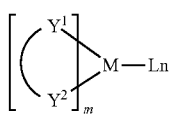

M is a metal having an atomic weight greater than 40; $(Y^1-Y^2)$ is a bidentate ligand, $Y^1$ and $Y^2$ are independently selected from C, N, C, P, and 5; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In one aspect, $(Y^1-Y^2)$ is a carbene ligand.

In one aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device in some embodiments of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host materials are preferred to have the following general formula:

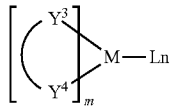

M is a metal; ($Y^3$-$Y^4$) is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

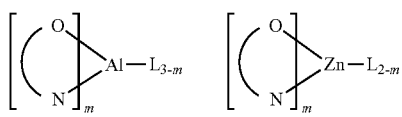

(O—N) is a bidentate ligand, having metal coordinated to atoms O and N.

In one aspect, M is selected from Ir and Pt.

In a further aspect, ($Y^3$-$Y^4$) is a carbene ligand.

Examples of organic compounds used as host materials include materials selected from the group consisting of: aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, sulfanyl, sulfinyl, sulfonyl, phosphino, and combinations thereof.

In one aspect, the host compound contains at least one of the following groups in the molecule:

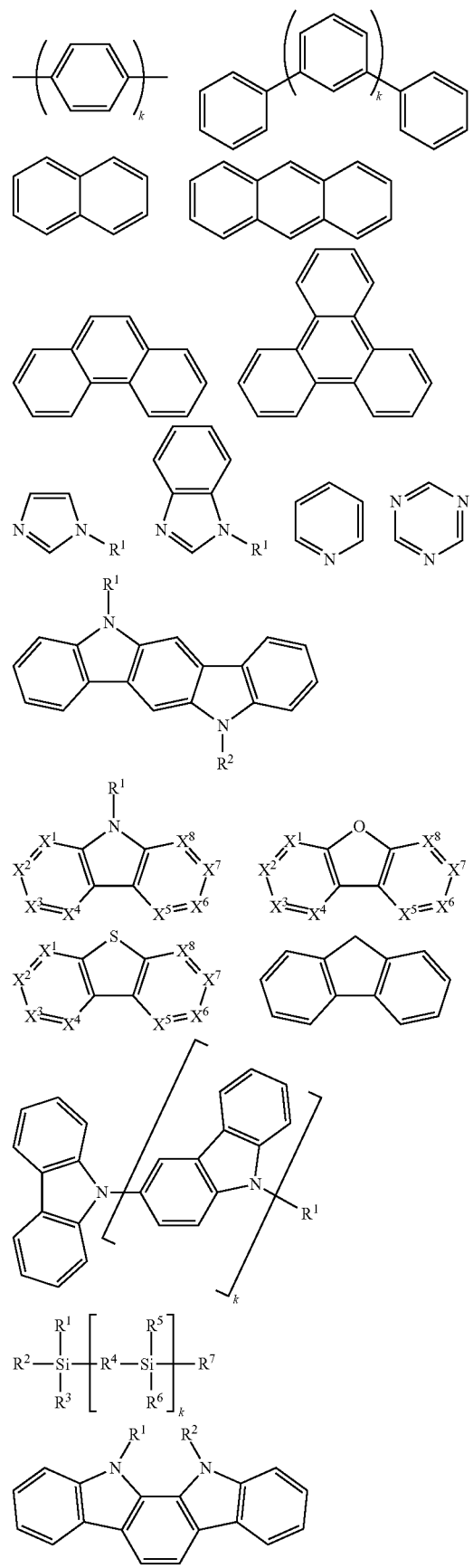

R[1] to R[7] is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

X[1] to X[8] is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, the compound used in the HBL contains the same molecule used as host described above.

In one aspect, the compound used in the HBL contains at least one of the following groups in the molecule:

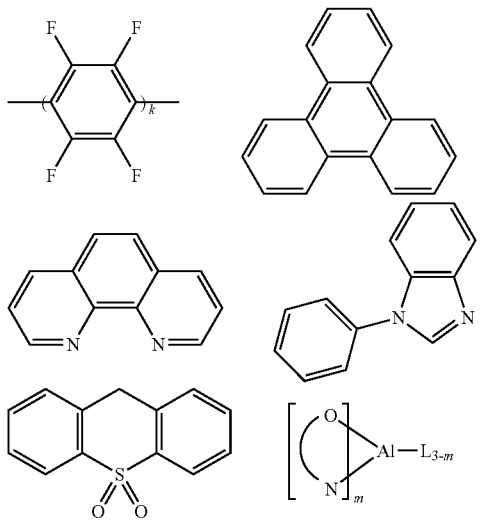

k is an integer from 0 to 20; L is an ancillary ligand, m is an integer from 1 to 3.

ETL:

The electron transport layer (ETL) may include a material capable of transporting electrons. The electron transport layer may be intrinsic (undoped) or doped. Doping may be used to enhance conductivity. Examples of the ETL material are not particularly limited, and any metal complexes or organic compounds may be used as long as they are typically used to transport electrons.

In one aspect, the compound used in the ETL contains at least one of the following groups in the molecule:

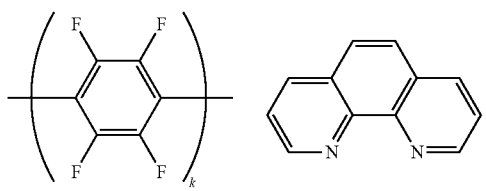

-continued

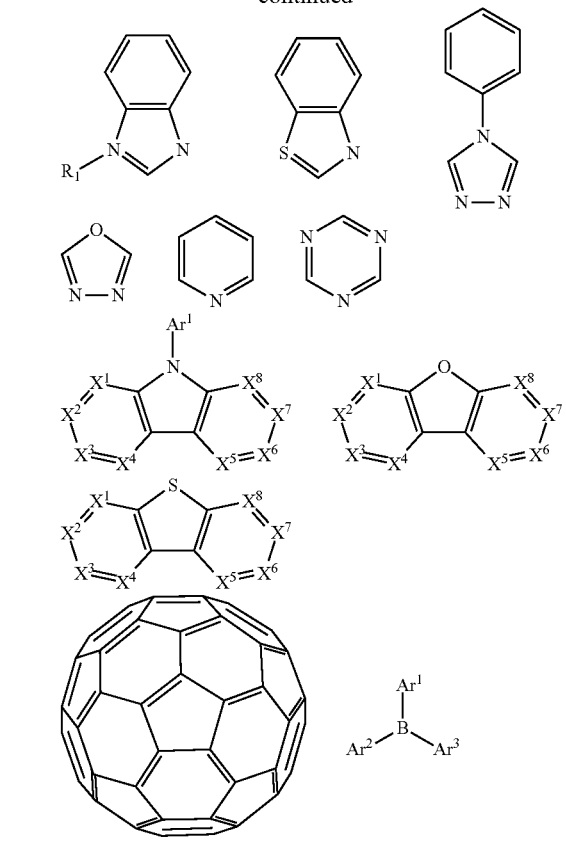

R[1] is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof, it has the similar definition as Ar's mentioned above.

Ar[1] to Ar[3] has the similar definition as Ar's mentioned above.

k is an integer from 0 to 20.

X[1] to X[8] is selected from CH or N.

In one aspect, the metal complexes used in the ETL may contain, but are not limit to, the following general formula:

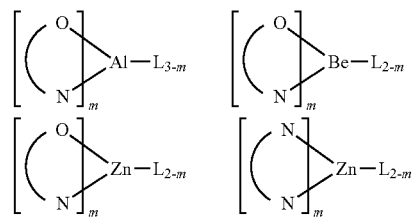

(O—N) or (N—N) is a bidentate ligand, having metal coordinated to atoms O, N or N,N; L is an ancillary ligand; m is an integer value from 1 to the maximum number of ligands that may be attached to the metal.

In any above-mentioned compounds used in each layer of OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATIONS |
| --- | --- | --- |
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and sliane SAMs | | US20030162053 |

TABLE 2-continued
| MATERIAL | EXAMPLES OF MATERIAL | PUBLICATIONS |
|---|---|---|
| Triarylamine or polythiophene polymers with conductivity dopants | 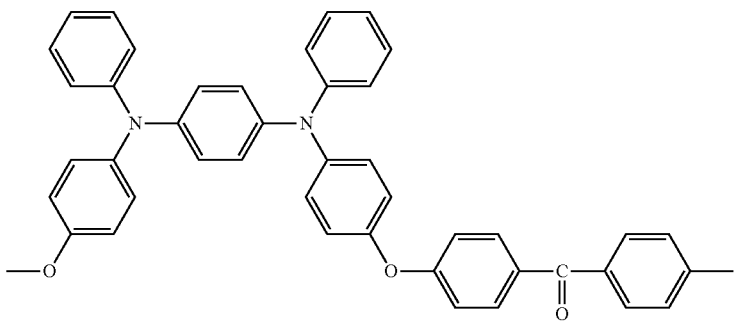 | EA01725079A1 |
| Arylamines complexed with metal oxides such as molybdenum and tungsten oxides | 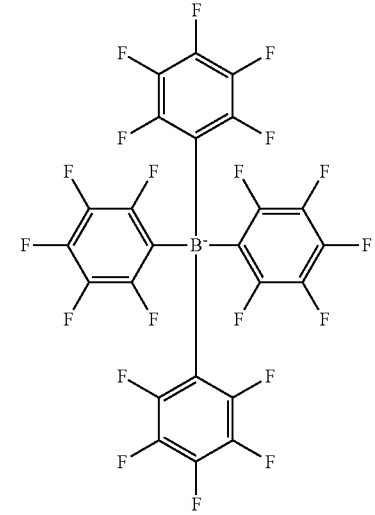 | SID Symposium Digest, 37, 923 (2006)<br>WO2009018009 |

| MATERIAL | EXAMPLES OF MATERIAL | PUBLICATIONS |
| --- | --- | --- |
| Semi-conducting organic complexes | | US20020158242 |
| Metal organometallic complexes | | US20060240279 |
| Cross-linkable compounds | | US20080220265 |
| Hole transporting materials | | |
| Triarylamines (e.g., TPD, α-NPD) | | Appl. Phys. Lett. 51, 913 (1987) |
| | | U.S. Pat. No. 5,061,569 |

TABLE 2-continued
| MATERIAL | EXAMPLES OF MATERIAL | PUBLICATIONS |
|---|---|---|
| | 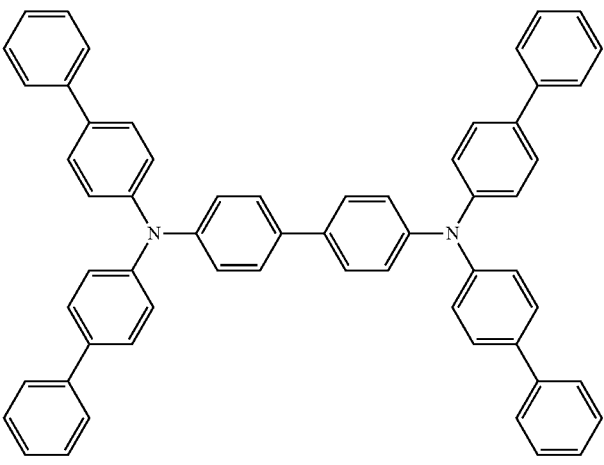 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 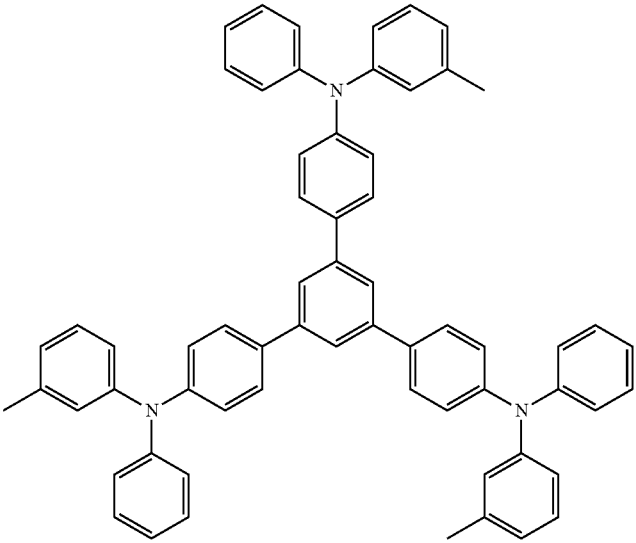 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 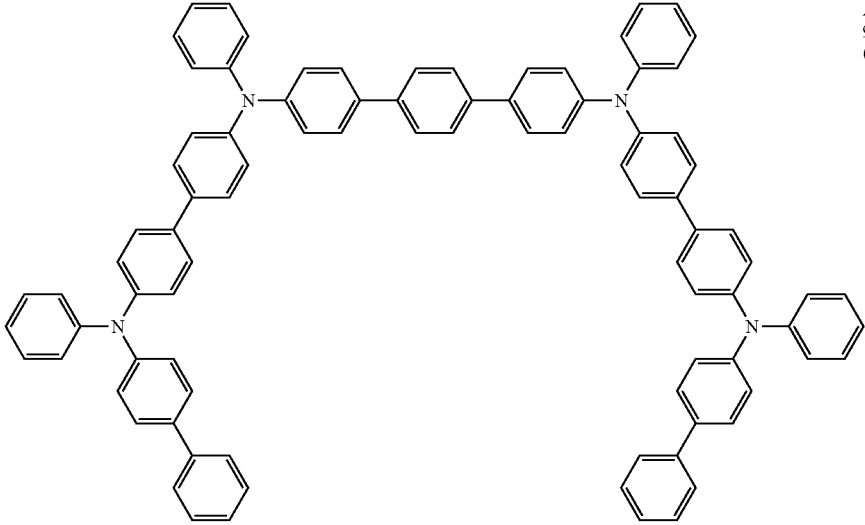 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 2-continued

| MATERIAL | EXAMPLES OF MATERIAL | PUBLICATIONS |
| --- | --- | --- |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzo-thiophene/ (di)benzofuran | | US20070278938, US20080106190 |

TABLE 2-continued

| MATERIAL | EXAMPLES OF MATERIAL | PUBLICATIONS |
| --- | --- | --- |
| Indolo-carbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Aryl-carbazoles | | Appl. Phys. Lett. 78, 1622 (2001) |

TABLE 2-continued
| MATERIAL | EXAMPLES OF MATERIAL | PUBLICATIONS |
|---|---|---|
| Metal 8-hydroxy-quinolates (e.g., Alq$_3$, BAlq) | 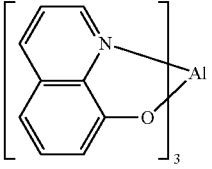 | Nature 395, 151 (1998) |
| | 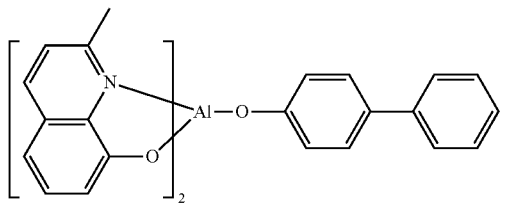 | US20060202194 |
| | 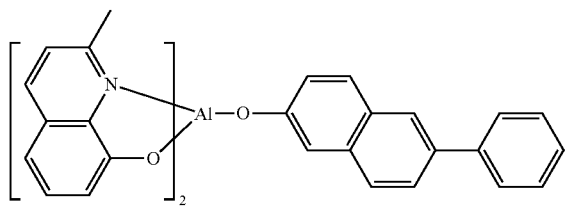 | WO2005014551 |
| | 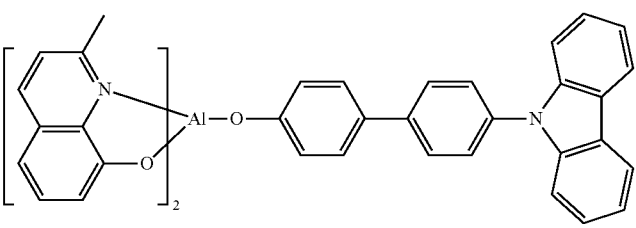 | WO2006072002 |
| Metal phenoxy-benzo-thiazole compounds | 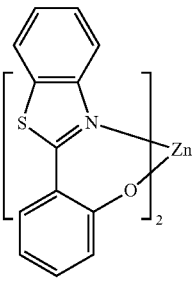 | Appl. Phys. Lett. 90, 123509 (2007) |
| Conugated oligomers and polymers (e.g., polyfluorene) | 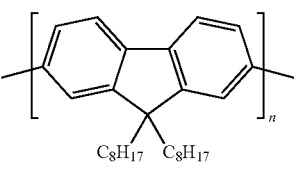 | Org. Electron. 1, 15 (2000) |
| Aromatic fused rings | 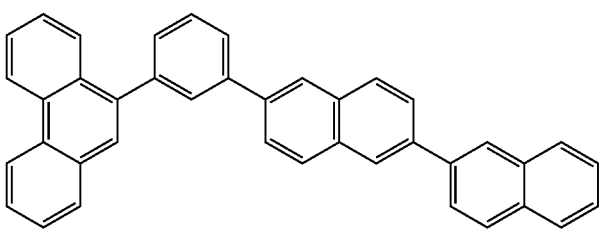 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |

TABLE 2-continued

| MATERIAL | EXAMPLES OF MATERIAL | PUBLICATIONS |
|---|---|---|
| Zinc complexes | | WO2009062578 |
| Green hosts | | |
| Aryl-carbazoles | | Appl. Phys. Lett. 78, 1622 (2001) |
| | | US20030175553 |
| | | WO2001039234 |
| Aryl-triphenylene compounds | | US20060280965 |

| MATERIAL | EXAMPLES OF MATERIAL | PUBLICATIONS |
|---|---|---|
| | 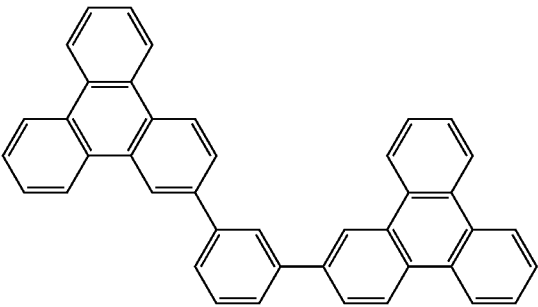 [SMILES: c1cc(-c2ccc3c4ccccc4c4ccccc4c3c2)cc(-c2ccc3c4ccccc4c4ccccc4c3c2)c1] | US20060280965 |
| | 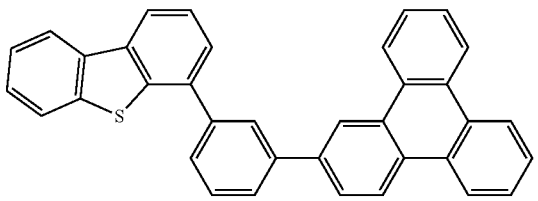 [SMILES: c1cc(-c2ccc3c4ccccc4c4ccccc4c3c2)cc(-c2cccc3c2sc2ccccc23)c1] | WO2009021126 |
| Donor acceptor type molecules | 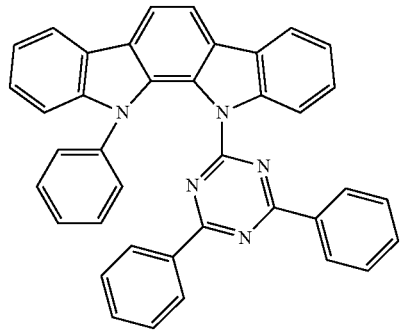 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/ DBT/DBF | 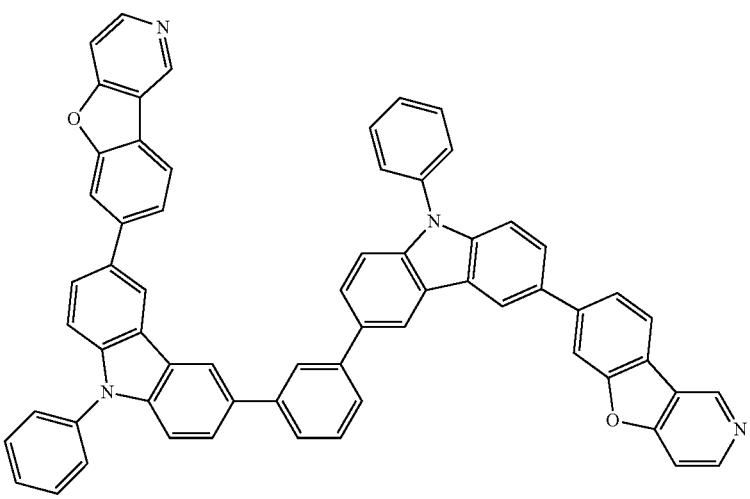 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 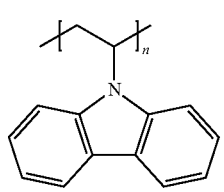 | Appl. Phys. Lett. 77, 2280 (2000) |

TABLE 2-continued
| MATERIAL | EXAMPLES OF MATERIAL | PUBLICATIONS |
|---|---|---|
| Spiro-fluorene compounds | 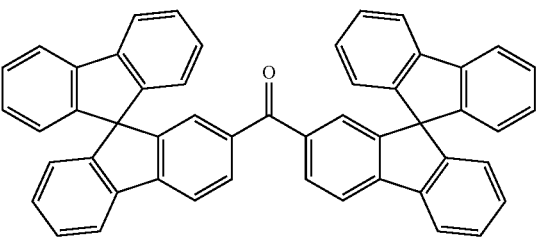 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxy-benzo-oxazole compounds | 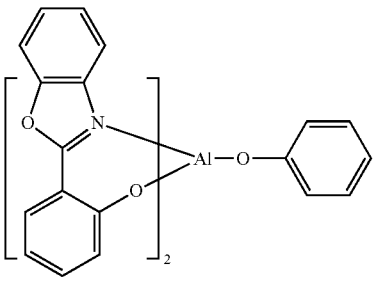 | WO2005089025 |
| | 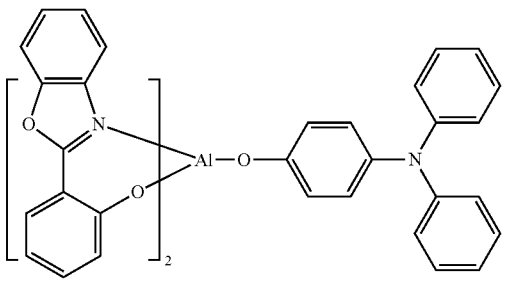 | WO2006132173 |
| | 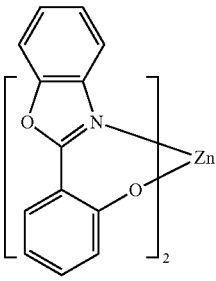 | JP200511610 |
| Spiro-fluorene-carbazole compounds | 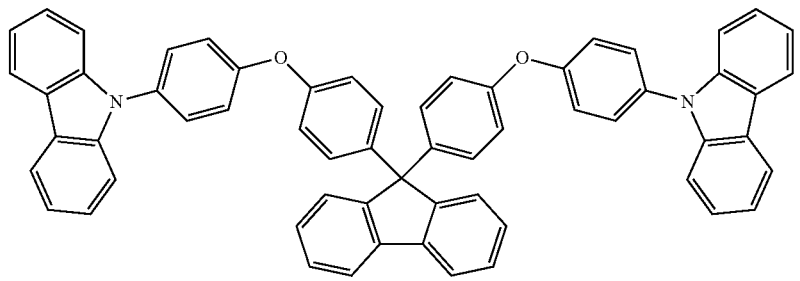 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 2-continued
| MATERIAL | EXAMPLES OF MATERIAL | PUBLICATIONS |
|---|---|---|
| | 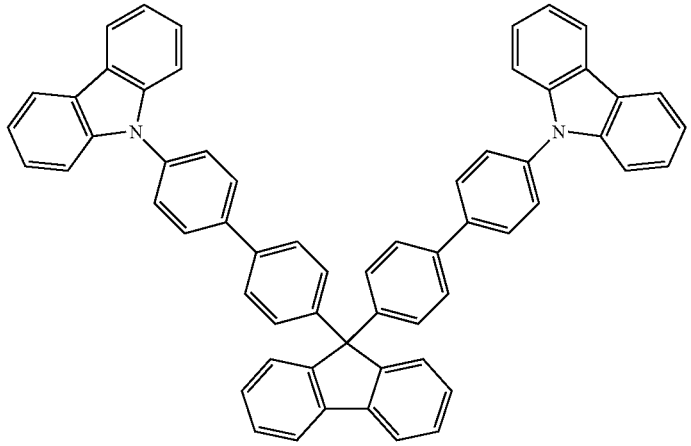 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolo-cabazoles | 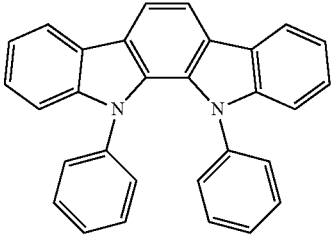 [SMILES: c1ccc(-n2c3ccccc3c3ccc4c5ccccc5n(-c5ccccc5)c4c32)cc1] | WO2007063796 |
| | 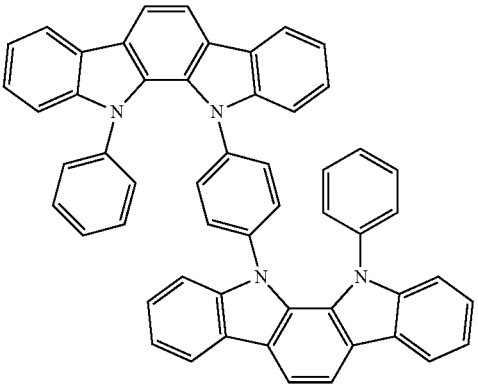 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 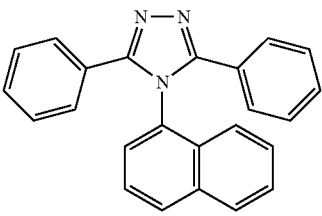 [SMILES: c1ccc(-c2nnc(-c3ccccc3)n2-c2cccc3ccccc23)cc1] | J. Appl. Phys. 90, 5048 (2001) |
| | 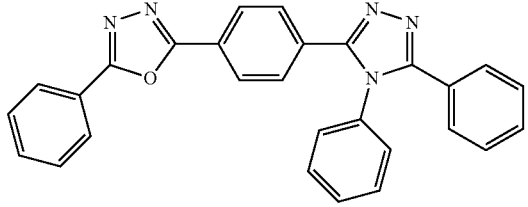 [SMILES: c1ccc(-c2nnc(-c3ccc(-c4nnc(-c5ccccc5)n4-c4ccccc4)cc3)o2)cc1] | WO2004107822 |

| MATERIAL | EXAMPLES OF MATERIAL | PUBLICATIONS |
|---|---|---|
| Tetra-phenylene complexes | 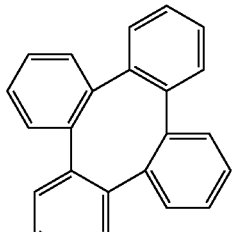 | US20050112407 |
| Metal phenoxy-pyridine compounds | 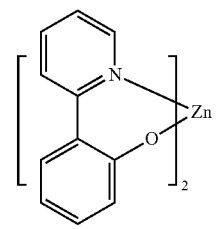 | WO2005030900 |
| Metal coordination complexes (e.g., Zn, Al with N^N ligands) | 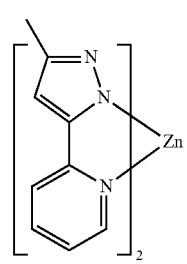 | US20040137268, US20040137267 |
Blue hosts
| | | |
|---|---|---|
| Aryl-carbazoles | 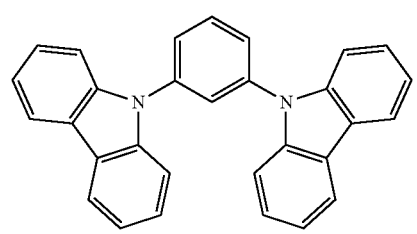 [SMILES: c1cc(-n2c3ccccc3c3ccccc32)cc(-n2c3ccccc3c3ccccc32)c1] | Appl. Phys. Lett, 82, 2422 (2003) |
| | 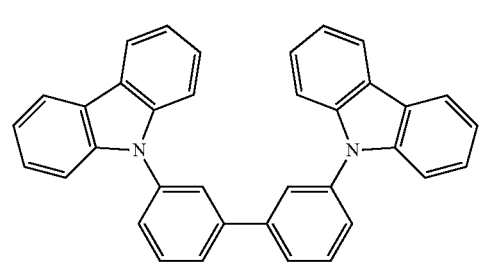 [SMILES: c1cc(-c2cccc(-n3c4ccccc4c4ccccc43)c2)cc(-n2c3ccccc3c3ccccc32)c1] | US20070190359 |

TABLE 2-continued
| MATERIAL | EXAMPLES OF MATERIAL | PUBLICATIONS |
|---|---|---|
| Dibenzo-thiophene/Dibenzo-furan-carbazole compounds | 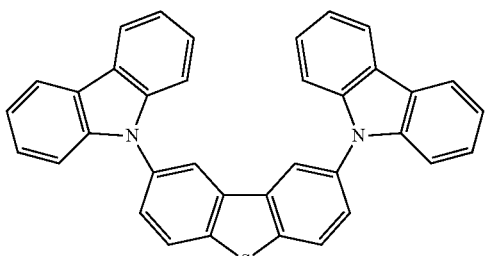 | WO2006114966, US20090167162 |
| | 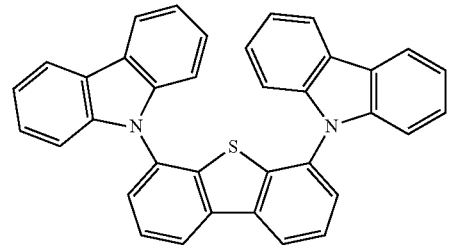 [SMILES: c1cc(-n2c3ccccc3c3ccccc32)c2sc3c(-n4c5ccccc5c5ccccc54)cccc3c2c1] | US20090167162 |
| | 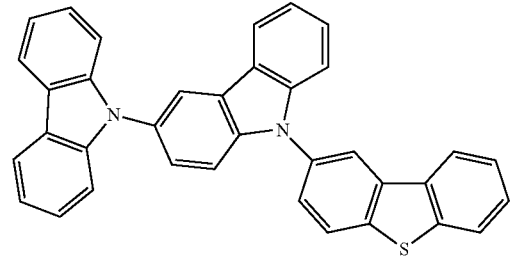 [SMILES: c1ccc2c(c1)sc1ccc(-n3c4ccccc4c4cc(-n5c6ccccc6c6ccccc65)ccc43)cc12] | WO2009086028 |
| | 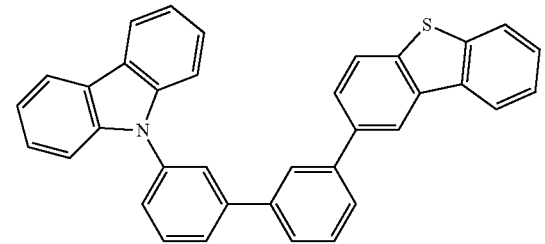 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 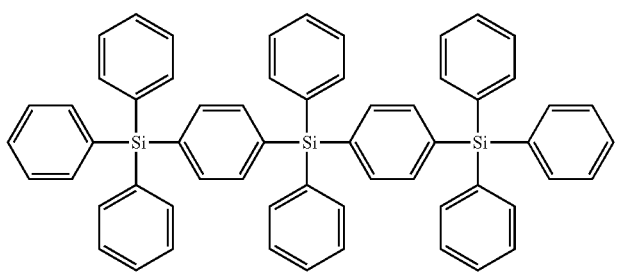 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 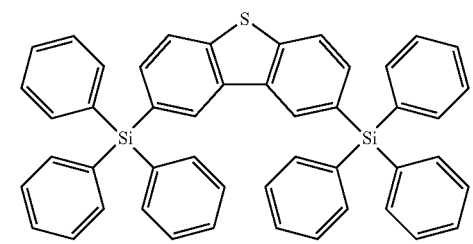 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | U.S. Pat. No. 7,154,114 |
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |

TABLE 2-continued

| MATERIAL | EXAMPLES OF MATERIAL | PUBLICATIONS |
| --- | --- | --- |
| | | US2006835469 |
| | | US2006835469 |
| | | US20060202194 |
| | | US20060202194 |
| | | US20070087321 |

TABLE 2-continued
| MATERIAL | EXAMPLES OF MATERIAL | PUBLICATIONS |
|---|---|---|
| | 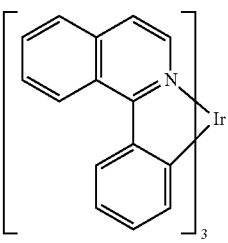 | US20070087321 |
| | 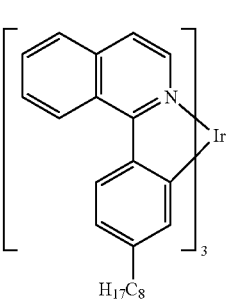 | Adv. Mater. 19, 739 (2007) |
| | 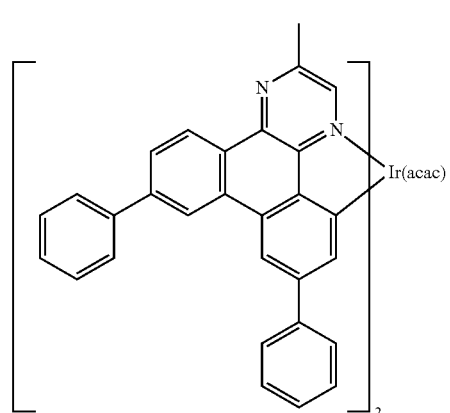 | WO2009100991 |
| | 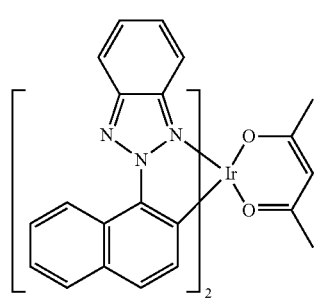 | WO2008101842 |
| Platinum(II) organo-metallic complexes | 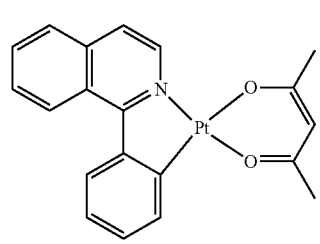 | WO2003040257 |

TABLE 2-continued

| MATERIAL | EXAMPLES OF MATERIAL | PUBLICATIONS |
|---|---|---|
| Osminum(III) complexes | [structure with F₃C-pyrazole-pyridine ligand and Os(PPhMe₂)₂] | Chem. Mater. 17, 3532 (2005) |
| Ruthenium(II) complexes | [structure with tBu-pyrazole-isoquinoline ligand and Ru(PPhMe₂)₂] | Adv. Mater. 17, 1059 (2005) |
| Rhenium (I), (II), and (III) complexes | [structure of quinolinolate-Re(CO)₄] | US20050244673 |
| Green dopants | | |
| Iridium(III) organometallic complexes | [structure of Ir(ppy)₃] and its derivatives | Inorg. Chem. 40, 1704 (2001) |
| | [structure of Ir(ppy)₂(acac)] | US20020034656 |

TABLE 2-continued

| MATERIAL | EXAMPLES OF MATERIAL | PUBLICATIONS |
|---|---|---|
| | | U.S. Pat. No. 7,332,232 |
| | | US20090108737 |
| | | US20090039776 |
| | | U.S. Pat. No. 6,921,915 |

TABLE 2-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670 JP2007123392 |
| | | Adv. Mater. 16, 2003 (2004) |

TABLE 2-continued

| MATERIAL | EXAMPLES OF MATERIAL | PUBLICATIONS |
|---|---|---|
|  |  | Angew. Chem. Int. Ed. 2006, 45, 7800 |
|  |  | WO2009050290 |
|  |  | US20090165846 |
|  |  | US20080015355 |
| Monomer for polymeric metal organometallic compounds |  | U.S. Pat. No. 7,250,226, U.S. Pat. No. 7,396,598 |

TABLE 2-continued
| MATERIAL | EXAMPLES OF MATERIAL | PUBLICATIONS |
|---|---|---|
| Pt(II) organo- metallic complexes, including polydentated ligands | 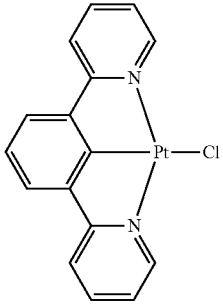 | Appl. Phys. Lett. 86, 153505 (2005) |
| | 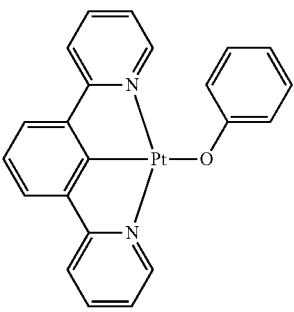 | Appl. Phys. Lett. 86, 153505 (2005) |
| | 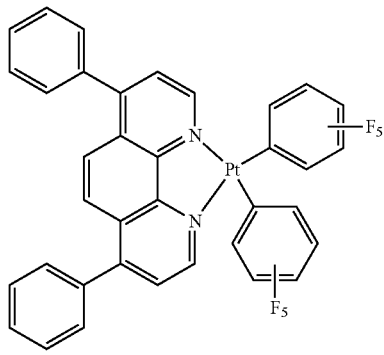 | Chem. Lett. 34, 592 (2005) |
| | 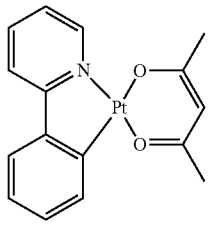 | WO2002015645 |
| | 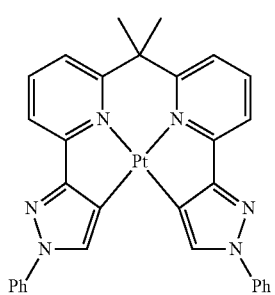 | US20060263635 |

TABLE 2-continued

| MATERIAL | EXAMPLES OF MATERIAL | PUBLICATIONS |
|---|---|---|
| Cu complexes | | WO2009000673 |
| Gold complexes | | Chem. Commum. 2906 (2005) |
| Rhenium(III) complexes | | Inorg. Chem. 42, 1248 (2003) |
| Deuterated organometallic complexes | | US20030138657 |

TABLE 2-continued

| MATERIAL | EXAMPLES OF MATERIAL | PUBLICATIONS |
|---|---|---|
| Organometallic complexes with two or more metal centers | | US20030152802 |
| | | U.S. Pat. No. 7,090,928 |
| Blue dopants | | |
| Iridium(III) organometallic complexes | | WO2002002714 |
| | | WO2006009024 |
| | | US20060251923 |

TABLE 2-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | U.S. Pat. No. 7,445,855 |
| | | US20070190359, US20080297033 |
| | | U.S. Pat. No. 7,338,722 |
| | | US20020134984 |

TABLE 2-continued

| MATERIAL | EXAMPLES OF MATERIAL | PUBLICATIONS |
|---|---|---|
| | | Angew. Chem. Int. Ed. 47, 1 (2008) |
| | | Chem. Mater. 18, 5119 (2006) |
| | | Inorg. Chem. 46, 4308 (2007) |
| | | WO20050123873 |
| | | WO2005123873 |
| | | WO2007004380 |

TABLE 2-continued
| MATERIAL | EXAMPLES OF MATERIAL | PUBLICATIONS |
|---|---|---|
| | 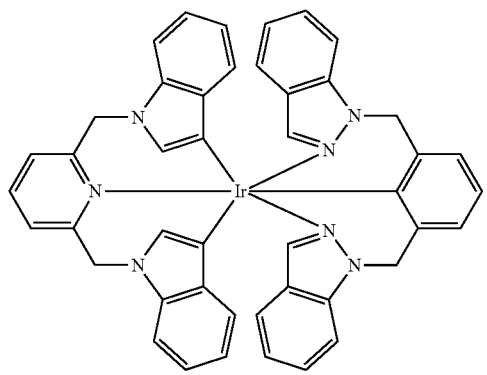 | WO2006082742 |
| Osmium(II) complexes | 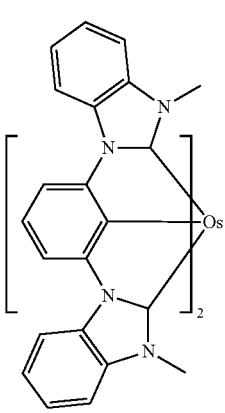 | U.S. Pat. No. 7,279,704 |
| | 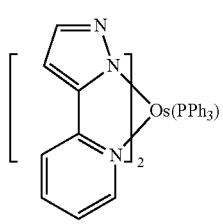 | Organometallics 23, 3745 (2004) |
| Gold complexes | 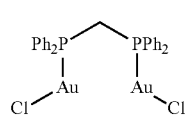 | Appl. Phys. Lett. 74, 1361 (1999) |
| Platinum(II) complexes | 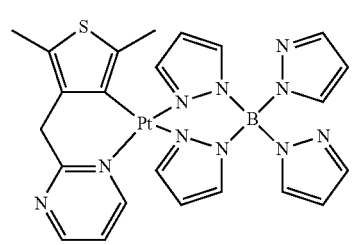 | WO2006098120, WO2006103874 |

TABLE 2-continued

| MATERIAL | EXAMPLES OF MATERIAL | PUBLICATIONS |
|---|---|---|
| Exciton/hold blocking layer materials | | |
| Bathocuprine compounds (e.g., BCP, BPhen) | 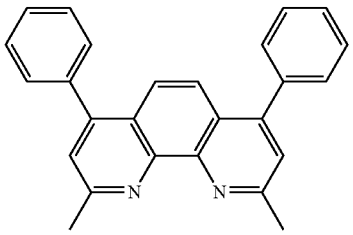 [SMILES: Cc1cc(-c2ccccc2)c2ccc3c(-c4ccccc4)cc(C)nc3c2n1] | Appl. Phys. Lett. 75, 4 (1999) |
| | 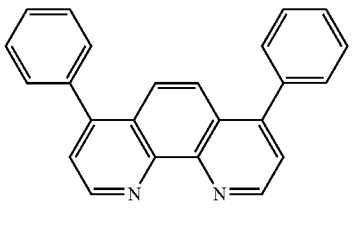 [SMILES: c1ccc(-c2ccnc3c2ccc2c(-c4ccccc4)ccnc23)cc1] | Appl. Phys. Lett. 79, 449 (2001) |
| Metal 8-hydroxy-quinolates (e.g., BAlq) | 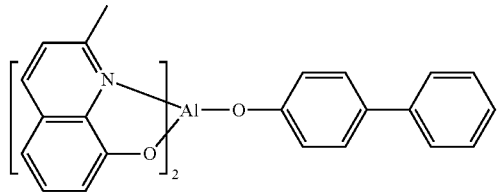 | Appl. Phys. Lett. 81, 162 (2002) |
| 5-member ring electron deficient heterocycles such as triazole, oxadiazole, imidazole, benzo-imidazole | 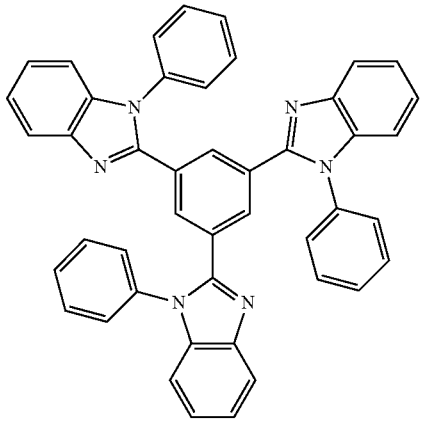 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 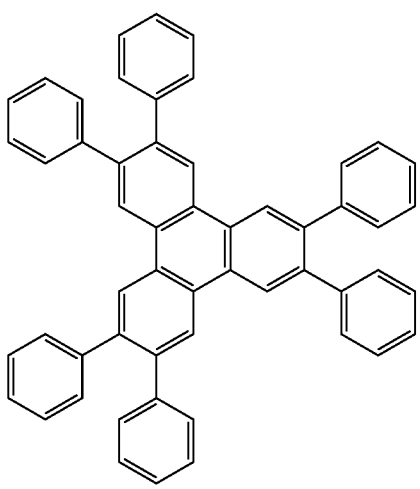 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 2-continued
| MATERIAL | EXAMPLES OF MATERIAL | PUBLICATIONS |
|---|---|---|
| Fluorinated aromatic compounds | 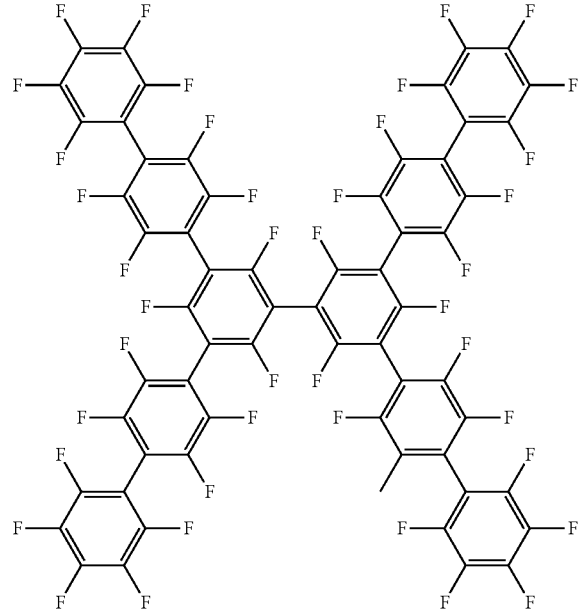 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 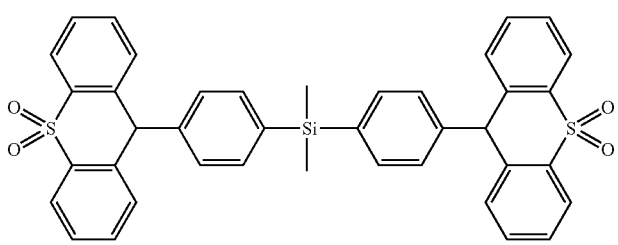 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO20080132085 |
| Electron transporting materials | | |
| Anthracene-benzoimidazole compounds | 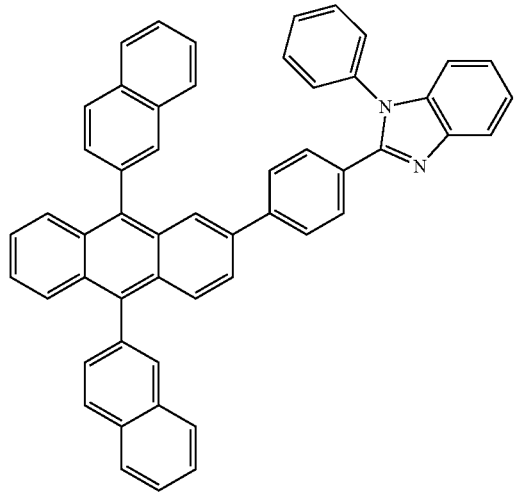 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 2-continued
| MATERIAL | EXAMPLES OF MATERIAL | PUBLICATIONS |
|---|---|---|
| | 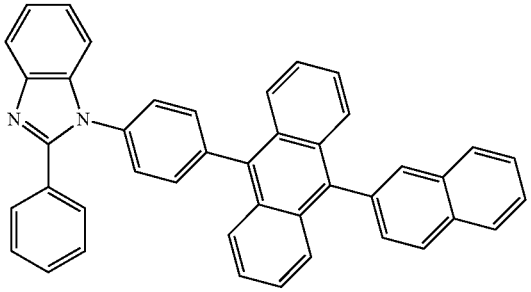 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 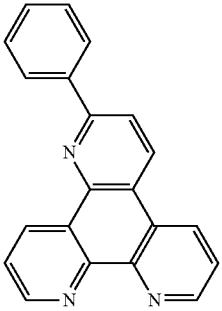 [SMILES: c1ccc(-c2ccc3c4cccnc4c4ncccc4c3n2)cc1] | US20090115316 |
| Anthracene-benzo-thiazole compounds | 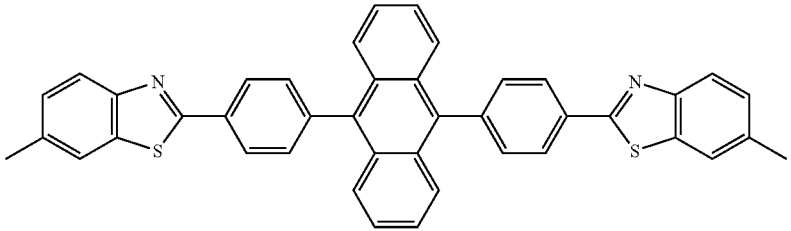 | Appl. Phys. Lett. 89, 063504 (2006) |
| Metal 8-hydroxy-quinolates (e.g., Alq$_3$, Zrq$_4$) | 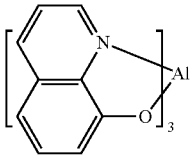 | Appl. Phys. Lett. 51, 913 (1987) U.S. Pat. No. 7,230,107 |
| Metal hydroxy-benzo-quinolates | 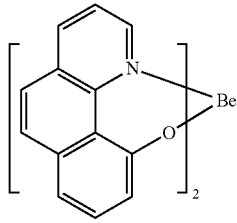 | Chem. Lett. 5, 905 (1993) |
| Bathocuprine compounds such as BCP, BPhen, etc | 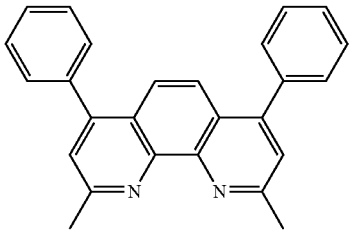 [SMILES: Cc1cc(-c2ccccc2)c2ccc3c(-c4ccccc4)cc(C)nc3c2n1] | Appl. Phys. Lett. 91, 263503 (2007) |

TABLE 2-continued
| MATERIAL | EXAMPLES OF MATERIAL | PUBLICATIONS |
|---|---|---|
| | 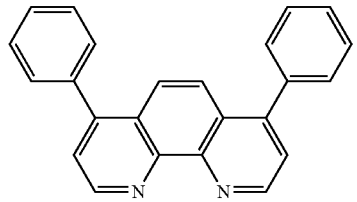 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzo-imidazole) | 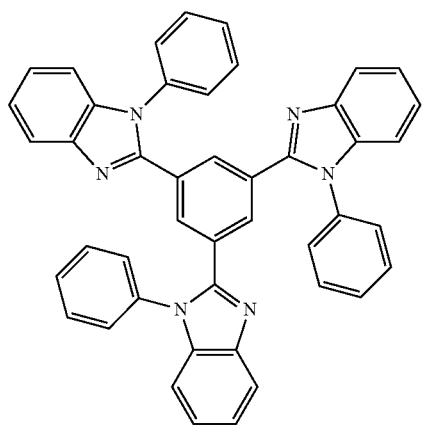 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 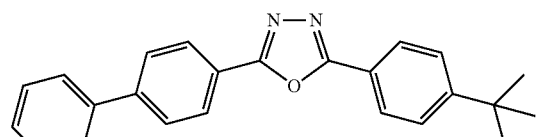 | Appl. Phys. Lett. 55, 1489 (1989) |
| | 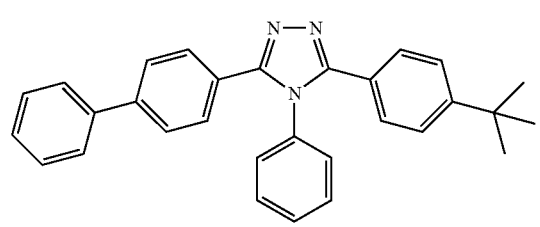 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 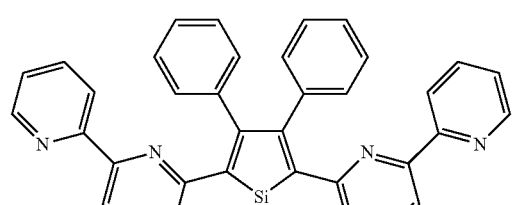 | Org. Electron. 4, 113 (2003) |
| Arylborane compounds | 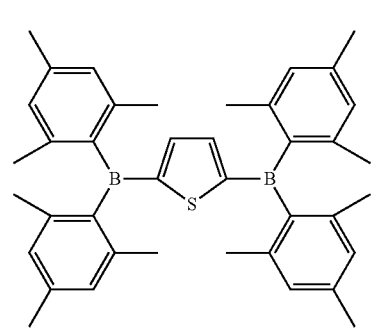 | J. Am. Chem. Soc. 120, 9714 (1998) |

TABLE 2-continued
| MATERIAL | EXAMPLES OF MATERIAL | PUBLICATIONS |
|---|---|---|
| Fluorinated aromatic compounds | 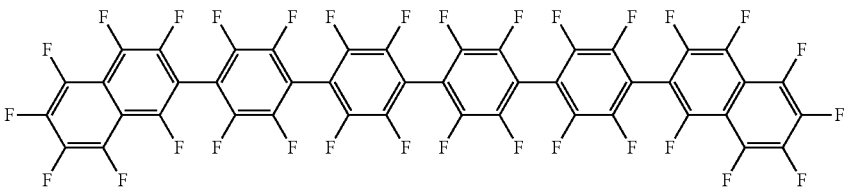 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 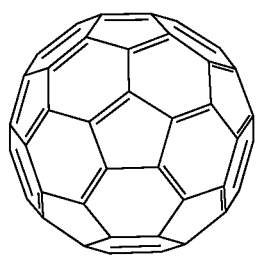 [SMILES: C1=CC2c3ccc4c5ccc6c7ccc8c9ccc%10c%11c%12c%13c%14c(c3c4c3c5c6c4c7c8c(c%119)c%13c4c%143)C2C%12C1%10] | US20090101870 |
| Triazine complexes | 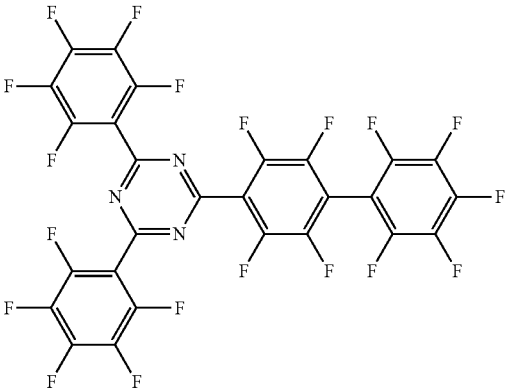 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 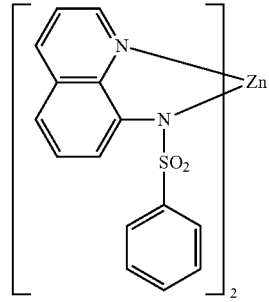 | U.S. Pat. No. 6,528,187 |

EXPERIMENTAL

Chemical abbreviations used throughout this document are as follows: DMF is dimethylformamide, Et$_3$N is triethylamine, PPh$_3$ is triphenylphosphine, P(i-Pr)$_3$ is triisopropylphosphine, EtOAc is ethyl acetate, THF is tetrahydrofuran, DMSO is dimethylsulfoxide, DCM is dichloromethane.

Example 1

Synthesis of Ruthenium Complex of Compound 33

Synthesis of 1,3-bis(1H-benzo[d]imidazol-1-yl)benzene

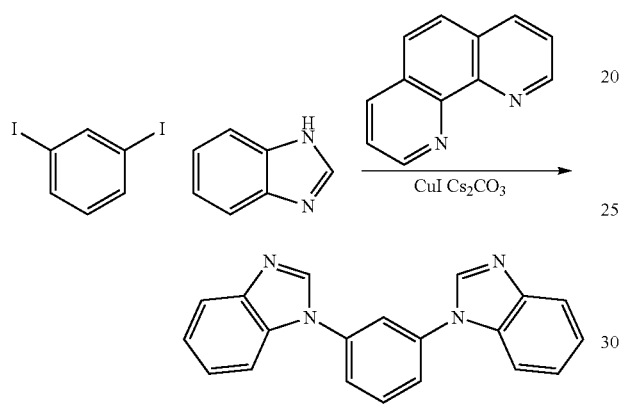

In a 1 L round-bottomed flask 1,3-diiodobenzene (26.43 g, 80 mmol), 1H-benzo[d]imidazole (20.82 g, 176 mmol), and 1,10-phenanthroline (5.77 g, 32.0 mmol), CuI (3.05 g, 16 mmol), and cesium carbonate (120 g, 369 mmol) were combined in anhydrous DMF (350 mL) to give a brown suspension. The reaction was purged with N$_2$ for 20 minutes and then heated to reflux for 24 hours. The reaction mixture was passed thought a plug of silica gel (5% MeOH in DCM) to obtain the crude product. The crude product was subjected to silica gel chromatography (SiO$_2$, 400 g, 2% MeOH to 5% MeOH in DCM) to ultimately obtain the final product (12.66 g, 51%).

Synthesis of 3,3'-(1,3-phenylene)bis(1-iodo-1-methyl-2,3-dihydro-1H-benzo[d]imidazol-1-ium-2-ide) [Compound 33]

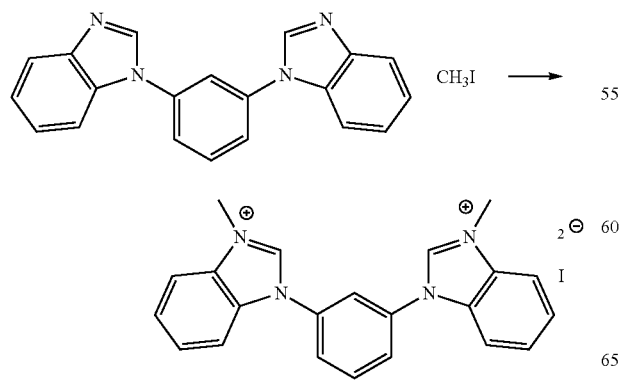

In a 1 L round bottom flask, 1,3-bis(1H-benzo[d]imidazol-1-yl)benzene (12.66 g, 40.8 mmol), iodomethane (25.5 mL, 408 mmol) were combined in DMF (500 mL) to give a yellow solution. The reaction mixture was heated to 42° C. for 24 hours and filtered to get the product (21.69 g, 89%).

Synthesis of Ruthenium Complex of Compound 33

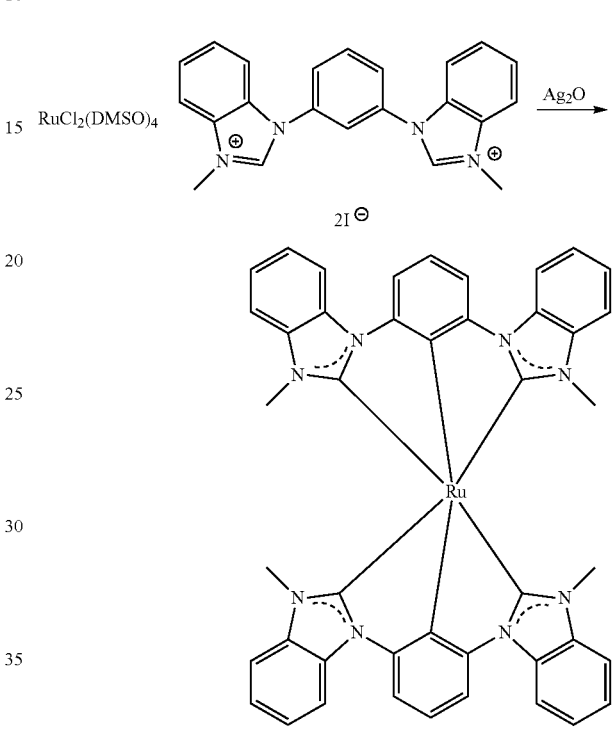

A 1 L round-bottomed flask was charged with RuCl$_2$(DMSO)$_4$ (2 g, 4.13 mmol), carbene ligand precursor compound 33 (7.36 g, 12.38 mmol), silver(I) oxide (5.74 g, 24.77 mmol) and 2-ethoxyethanol (400 mL) to give a tan suspension. The reaction mixture was vacuum evacuated, backfilled with N$_2$ and heated to reflux for 1 hour. The reaction mixture was filtered and the filtrate was evaporated to dryness. The residue obtained after evaporation was subjected to column chromatography (SiO$_2$, pretreated with Et$_3$N, 50% DCM in hexanes) to yield the ruthenium complex of compound 1 (1070 mg, 33%).

Synthesis of 1,3-bis(3H-imidazo[4,5-b]pyridin-3-yl)benzene

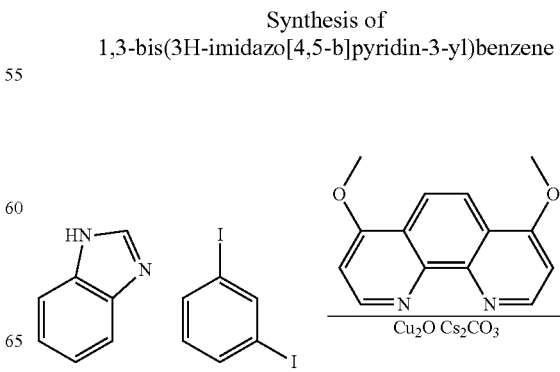

-continued

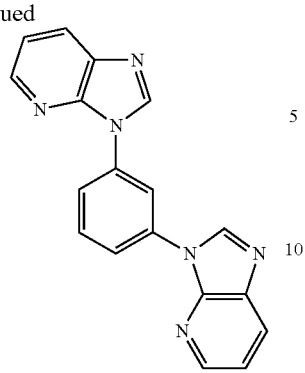

A 500 mL round-bottomed flask was charged with 1H-imidazo[4,5,-b]pyridine (12.7 g, 107 mmol), 1,3-diiodobenzene (17.65 g, 53.5 mmol), copper (1) oxide (0.176 g, 1.231 mmol), 4,7-dimethoxy-1,10-phenanthroline (0.591 g, 2.46 mmol), cesium carbonate (48.8 g, 150 mmol), polyethylene glycol (9.79 g, D=1.088, 9 mL) and DMSO (125 mL). The reaction mixture was vacuum evacuated and back filled with N₂ three times. The reaction mixture was heated to 110° C. for 24 hours. The reaction mixture was decanted into water (500 mL) and filtered. The precipitate was collected subjected to column chromatography (SiO₂, 5% MeOH in DCM) to yield the desired product (6 g, 36%).

Synthesis of Ruthenium Complex of Compound 53

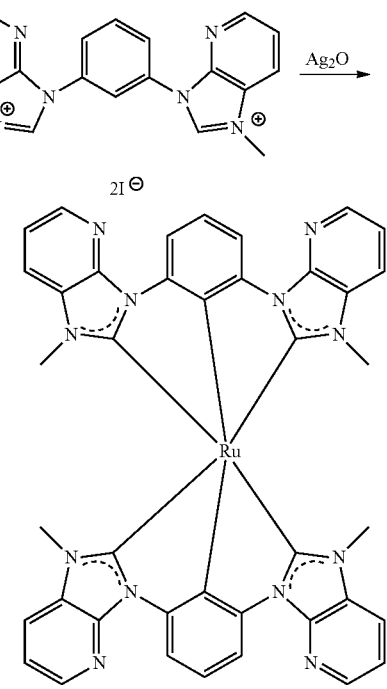

A 1 L round-bottomed flask was charged with carbene precursor compound 53 (2.98 g, 4.99 mmol), Ag₂O (2.31 g, 9.99 mmol) and 2-ethoxyethanol (390 mL). The reaction mixture was vacuum evacuated and back filled with N₂ three times. The reaction mixture was heated to for 1 hour. The Ru precursor (1.1 g, 2.27 mmol) was then added and the reaction mixture was refluxed for 1 hour. The reaction mixture was filtered and the filtrate was evaporated to dryness. The residue obtained after evaporation was subjected to column (SiO₂, pretreated with Et₃N, 70% DCM in hexanes) to yield the title complex (0.82 g, 46%).

Synthesis of OsCl₂(DMSO)₄

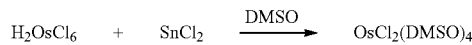

An aqueous solution of [NH₄]₂[OsCl₆] (1 g, 2.278 mmol) was passed through a cation exchange column in the protic form, eluted with water, after which the solvent was removed from the eluate using a rotatory evaporator. The residue was transferred to a Schlenk tube as a solution in methanol and the solvent removed in vacuo. The resulting red-black residue was dissolved in DMSO (5 mL), and SnCl₂.2H₂O (0.8 g, 3.55 mmol) was added and the mixture was stirred under N₂ for 1 hour at 150° C. The DMSO was removed by vacuum distillation. 20 mL of DCM was added into the residue and the suspension was filtered through celite. The filtrate was concentrated and washed with acetone to yield the desired compound (0.7 g, 53.6%)

Synthesis of OsCl₂(PPh₃)₃

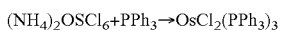

(NH₄)₂OsCl₆ (2.57 g, 5.85 mmol) and PPh₃ (10.82 g, 41.2 mmol) were refluxed under nitrogen for 20 hours in a solvent mixture composed of 385 mL tert-butyl alcohol and 154 mL water. After cooling to room temperature, the pale green solid was filtered, washed with water, methanol, and hexanes. The solid was dried under vacuum to yield the desired product (5.65 g, 92%).

Synthesis of OsH₆(P(i-Pr)₃)₂

Step 1

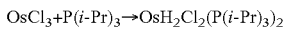

A suspension of OsCl₃ (3.79 g, 12.77 mmol) in 40 mL of 2-propanol was treated with P(i-Pr)₃ (12 g, 90% purity, 67.4 mmol) and heated for 24 hours under reflux. After the mixture was cooled to room temperature, a brown-yellow precipitate was formed, which was filtered off, and repeatedly washed with methanol and ether, and dried in vacuo to yield OsH₂Cl₂(P(i-Pr)₃)₂ (2.11 g, 28.3%)

Step 2

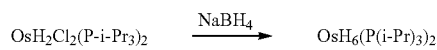

A solution of OsH₂Cl₂(P(i-Pr)₃)₂ in 180 mL of toluene was first treated with NaBH₄ (1.737 g, 45.9 mmol) and then dropwise with 5 mL of methanol. After the reaction mixture was stirred for 30 minutes at room temperature, the solution was filtered. The filtrate was concentrated to ca 0.5 mL in vacuo, and 10 mL of methanol was added. The solution was again concentrated until a white precipitate separated and then stored at −78° C. for 2 hours. The white precipitate was filtered off, washed with small amount of methanol, and dried in vacuo: yield 0.37 g (15.6%).

Synthesis of [OsCl$_2$(benzene)]$_2$

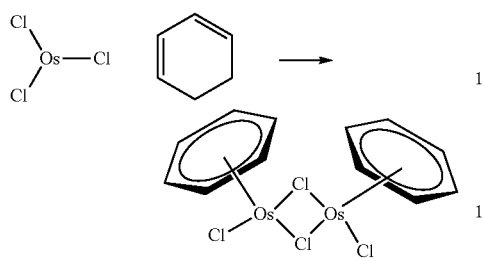

A suspension of OsCl$_3$ (7.85 g, 26.5 mmol) in 100 mL of ethanol was treated with cyclohexa-1,3-diene (2.12 g, 26.5 mmol) and heated for 48 hours under reflux. The yellow precipitate was filtered off, washed with a small amount of methanol, and dried in vacuo: yield 7.26 g (81%).

Methods for Osmium Ligation Using Compound 35
Method A

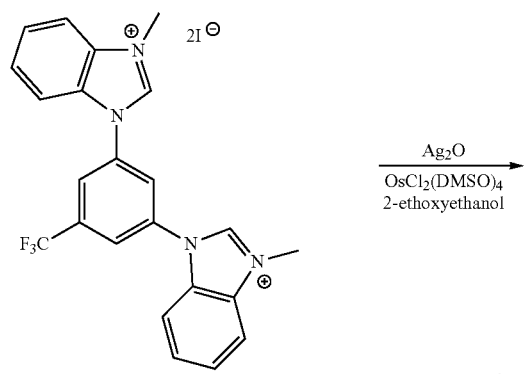

A 250 mL round-bottomed flask was charged with OsCl$_2$(DMSO)$_4$ (250 mg, 0.436 mmol), tridentate carbene precursor compound 35 (721 mg, 1.089 mmol), and silver (I) oxide (505 mg, 2.179 mmol) in 2-ethoxyethanol (125 mL) to give a tan suspension. The reaction mixture was vacuum evacuated, back filled with N$_2$ and heated to reflux for 1 hour. The reaction mixture was filtered thought celite and the filtrate was subject to column chromatography (SiO$_2$, pretreated with Et$_3$N, 60% EtOAc in hexanes) to yield the desired compound (152 mg, 34%).

Method B

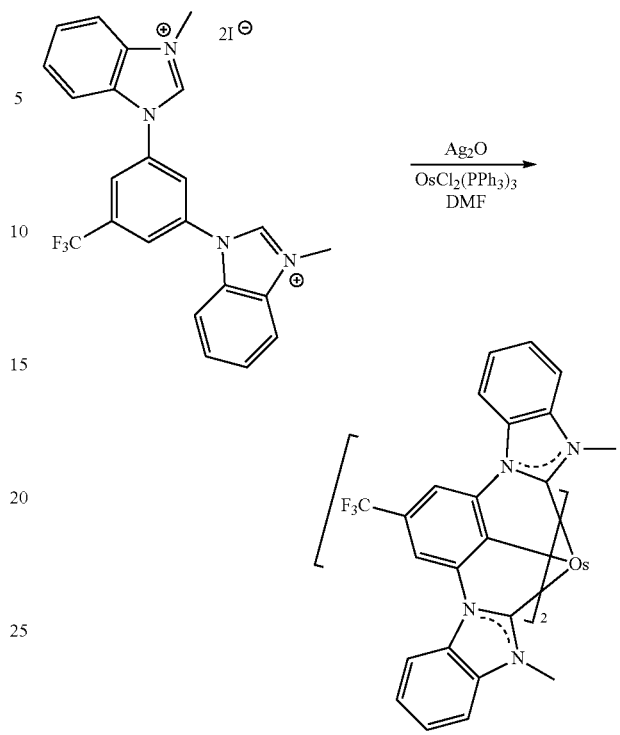

A 250 mL round-bottomed flask was charged with OsCl$_2$(PPh$_3$)$_4$ (250 mg, 0.436 mmol), tridentate carbene precursor compound 35 (721 mg, 1.089 mmol), and silver (I) oxide (505 mg, 2.179 mmol) in DMF (125 mL) to give a tan suspension. The reaction mixture was vacuum evacuated, back filled with N$_2$, and heated to reflux for 1 hour. The reaction mixture was filtered thought celite and the filtrate was subject to column chromatography (SiO$_2$, pretreated with Et$_3$N, 60% EtOAc in hexanes) to yield the desired compound (17 mg, 4%).

Method C

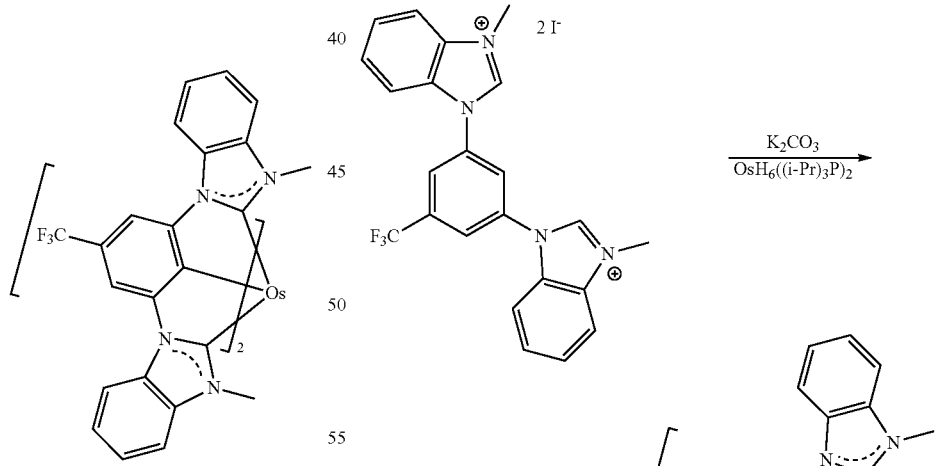

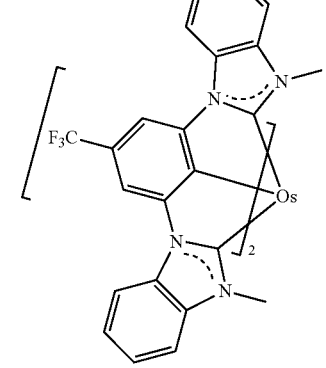

A 250 mL round-bottomed flask was charged with OsH$_6$((i-Pr)$_3$P)$_2$ (150 mg, 0.29 mmol), tridentate carbene precursor compound 35 (404 mg, 0.61 mmol) and K$_2$CO$_3$ (401 mg, 2.9 mmol) in dioxane (100 mL) to give a tan suspension. The reaction mixture was vacuum evacuated, back filled with N$_2$ and heated to reflux for 7 hours. The reaction mixture was filtered thought celite and the filtrate was subject to column chromatography (SiO$_2$, pretreated with Et$_3$N, 30% DCM in hexanes) to yield desired compound (51 mg, 12%).

Method D

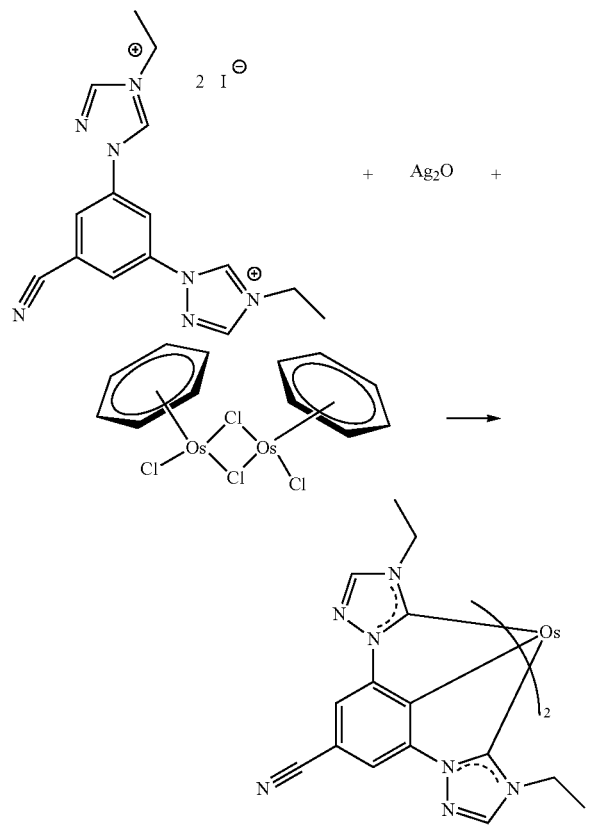

A 1 L round-bottomed flask was charged with silver (I) oxide (9.9 9 g, 43.1 mmol), tridentate carbene precursor compound 75 (11.84 g, 21.56 mmol) and DMF (700 mL). The reaction mixture was vacuum evacuated and back filled with N$_2$. It was stirred for 1 hour at room temperature. The reaction mixture was filtered thought celite and the filtrate was treated with [OsCl$_2$(benzene)]$_2$ (3.66 g, 5.39 mmol). The reaction mixture was heated to 120° C. for 2 hours. The DMF was then removed by vacuum distillation, and the residue was subjected to column chromatography (SiO$_2$, pretreated with Et$_3$N, EtOAc) to yield desired compound (334 mg, 4%).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A method of making a metal complex having the formula I, $$Q_1\text{-}M\text{-}Q_2,$$

the method comprising:
mixing a salt of formula MX$_2$L$_n$ with precursors of carbenes Q$_1$ and Q$_2$, wherein Q$_1$ and Q$_2$ are independently selected from a compound of formula II,

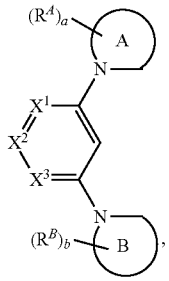

a carbene forming agent, a solvent, resulting in a reaction mixture, and
heating the reaction mixture, wherein:
M is a second or third row transition metal in the +2 oxidation state;
X is a halogen;
L is a ligand coordinated to M and selected from the group consisting of DMSO, THF, and CH$_3$CN;
n is from 2 to 4;
wherein ring A is selected from the group consisting of:
   (a) a 5-membered heterocyclic group;
   (b) an 8- to 12-membered bicyclic group having from 0 to 6 ring heteroatoms;
   (c) an 11- to 18-membered tricyclic group having from 0 to 7 ring heteroatoms;
   (d) an 11- to 14-membered fused tricyclic group having from 0 to 6 ring heteroatoms; and
   (e) an 14- to 18-membered fused tetracyclic group having from 0 to 7 ring heteroatoms;
wherein ring A may form a salt;
a is 0 to 4;
wherein ring B is selected from the group consisting of:
   (a) a 5-membered heterocyclic group;
   (b) an 8- to 12-membered bicyclic group having from 0 to 6 ring heteroatoms;
   (c) an 11- to 18-membered tricyclic group having from 0 to 7 ring heteroatoms;
   (d) an 11- to 14-membered fused tricyclic group having from 0 to 6 ring heteroatoms; and
   (e) a 14- to 18-membered fused tetracyclic group having from 0 to 7 ring heteroatoms;
wherein ring B may form a salt;
b is 0 to 4;
X$^1$ is selected from C—R$^1$ and N;
X$^2$ is selected from C—R$^2$ and N;
X$^3$ is selected from C—R$^3$ and N;
optionally, R$^1$ and R$^2$, or R$^2$ and R$^3$ are linked to form a 5- or 6-membered cyclic group, an 8- to 10-membered fused bicyclic group, an 11- to 14-membered fused tricyclic group, which may be optionally substituted with one or more substituents independently selected from hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

optionally, $R^1$ and an $R^A$ are linked to form a 5- or 6-membered cyclic group, or an 8- to 10-membered fused bicyclic group;

optionally, $R^3$ and an $R^B$ are linked to form a 5- or 6-membered cyclic group, or an 8- to 10-membered fused bicyclic group;

wherein $R^A$, $R^B$, $R^1$, $R^2$, and $R^3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

2. The method of claim 1, wherein M is Ru or Os.

3. The method of claim 1, wherein the carbene forming agent is selected from silver(I) oxide and copper(I) alkoxide.

4. The method of claim 3, wherein the copper(I) alkoxide is copper(I) tert-butoxide.

5. The method of claim 2, wherein M is Ru, L is DMSO, and n is 4.

6. The method of claim 5, wherein X is Cl.

7. The method of claim 2, wherein M is Os, L is DMSO, and n is 4.

8. The method of claim 7, wherein X is Cl.

9. The method of claim 2, wherein the solvent comprises a polar solvent.

10. The method of claim 9, wherein the polar solvent comprises an alcohol.

11. The method of claim 10, wherein the alcohol is selected from the group consisting of 2-methoxyethanol, 2-ethoxyethanol, and mixtures thereof.

12. The method of claim 2, wherein precursors of carbenes Q1 and Q2 is independently selected from a compound of formula III:

wherein:
the dashed line represents an optional bond;
$X^4$ is selected from N—R', O, and S;
$X^5$ is selected from N—R', O, and S;
R' is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
A is a counterion.

13. The method of claim 12, wherein the carbene precursor is selected from the group consisting of:

Compound 5
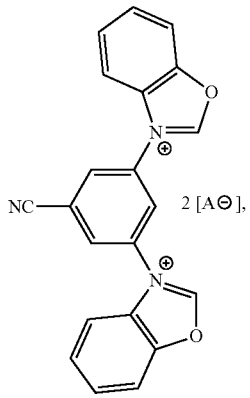
Compound 6
Compound 7
Compound 8
Compound 9
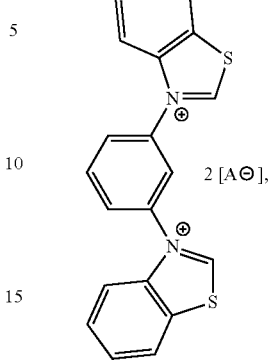
Compound 10
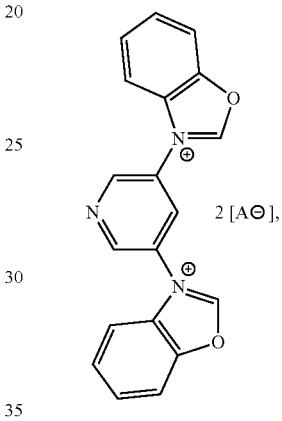
Compound 11
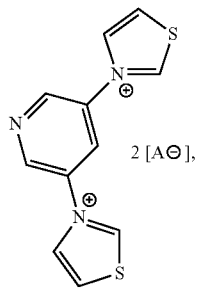
Compound 12
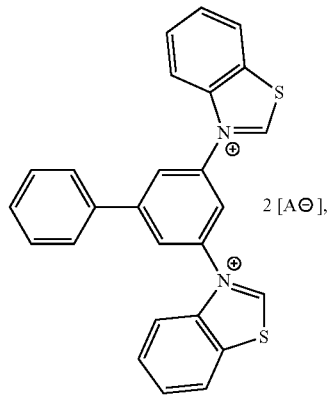

Compound 13
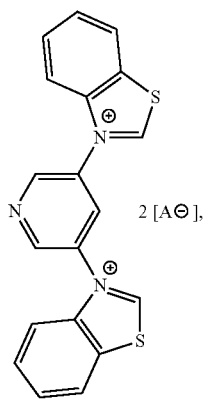
2 [A⊖],
Compound 17
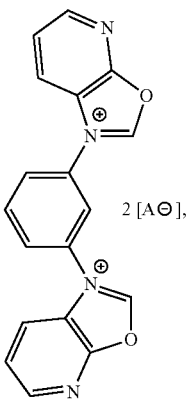
2 [A⊖],
Compound 14
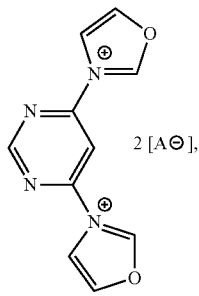
2 [A⊖],
Compound 18
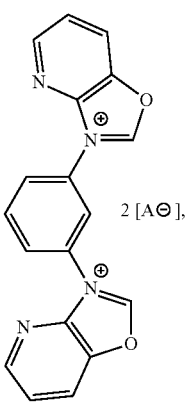
2 [A⊖],
Compound 15
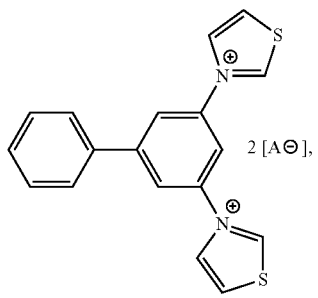
2 [A⊖],
Compound 19
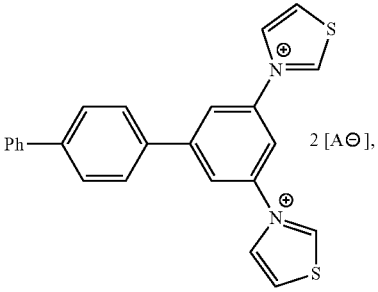
2 [A⊖],
Compound 16
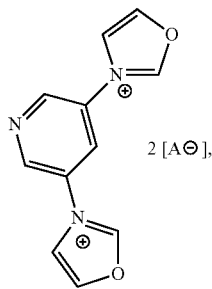
2 [A⊖],
Compound 20
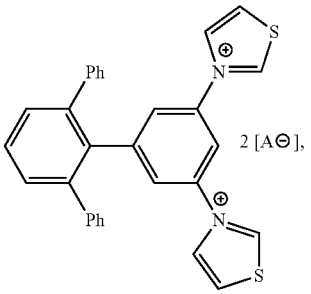
2 [A⊖], Compound 21
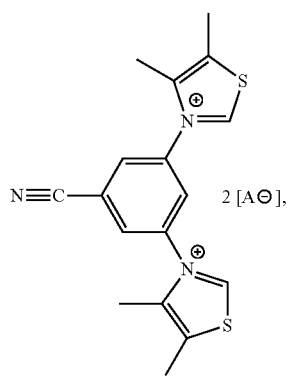 2 [A⊖],
Compound 25
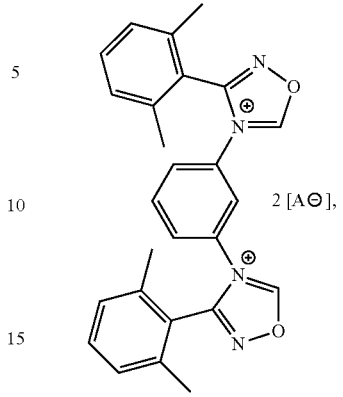 2 [A⊖],
Compound 22
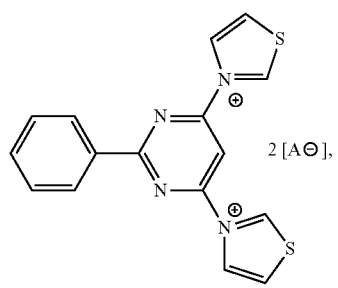 2 [A⊖],
Compound 26
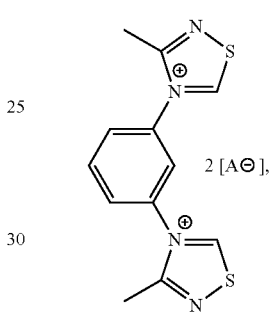 2 [A⊖],
Compound 23
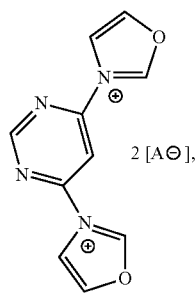 2 [A⊖],
Compound 27
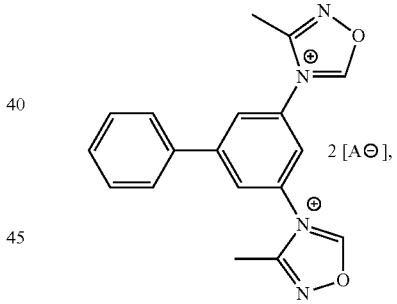 2 [A⊖],
Compound 24
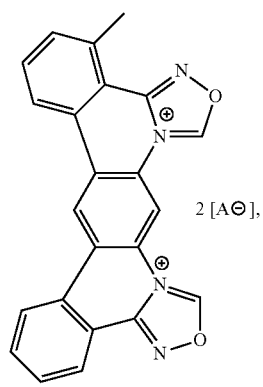 2 [A⊖],
Compound 28
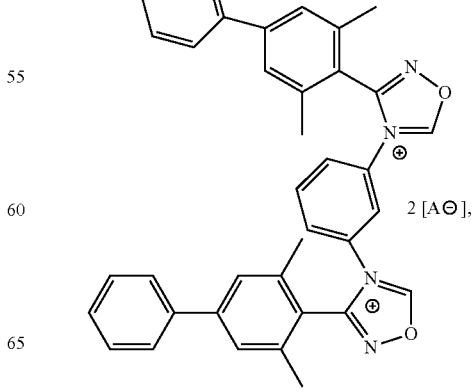 2 [A⊖], Compound 29
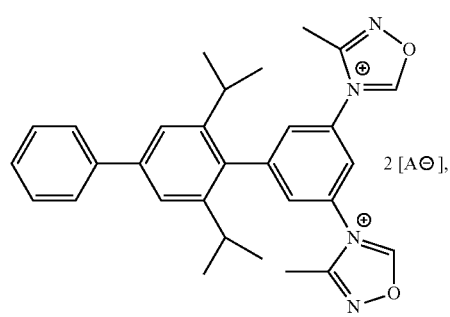
2 [A⊖],
Compound 30
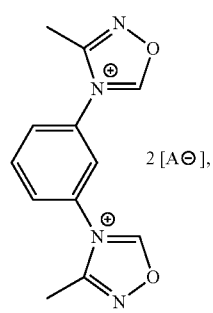
2 [A⊖],
Compound 31
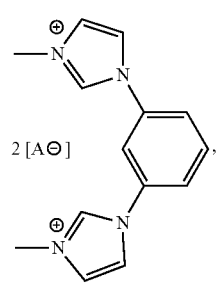
2 [A⊖],
Compound 32
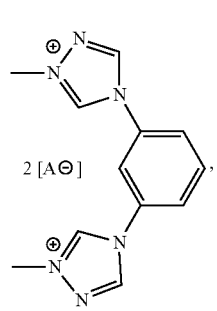
2 [A⊖],
Compound 33
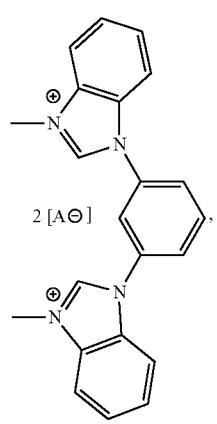
2 [A⊖],
Compound 34
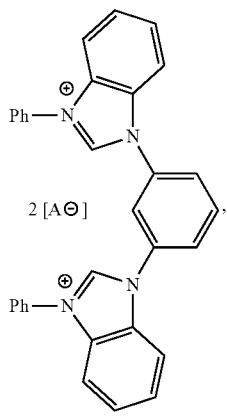
2 [A⊖],
Compound 35
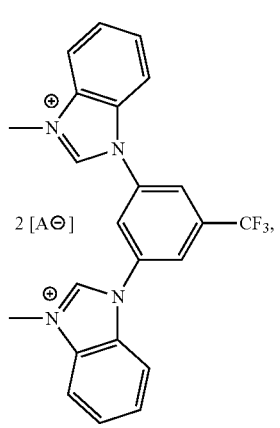
2 [A⊖],
Compound 36
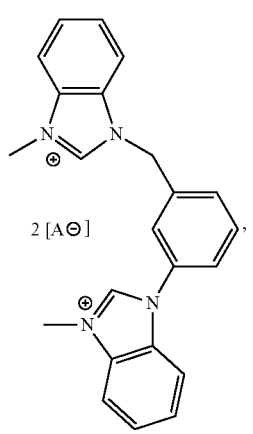
2 [A⊖],
Compound 37
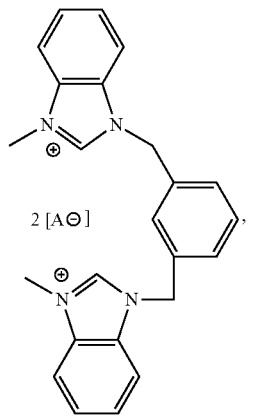
2 [A⊖], -continued
Compound 38
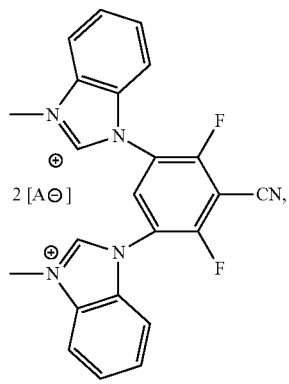
2 [A⊖]
Compound 39
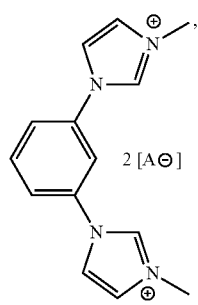
2 [A⊖]
Compound 40
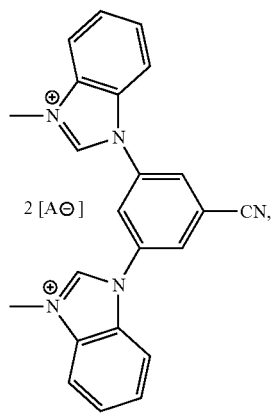
2 [A⊖]
Compound 41
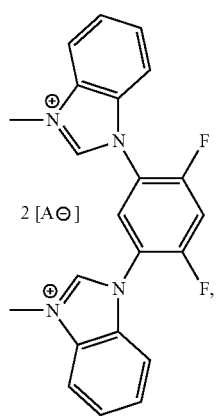
2 [A⊖]
-continued
Compound 42
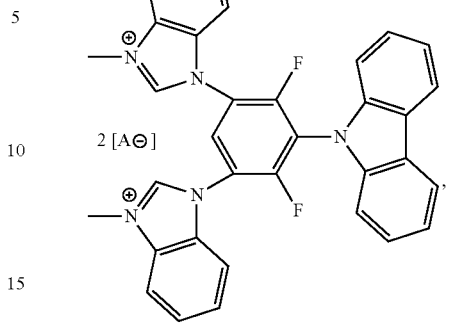
2 [A⊖]
Compound 43
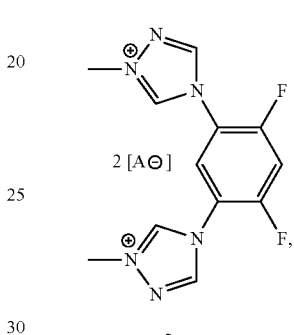
2 [A⊖]
Compound 44
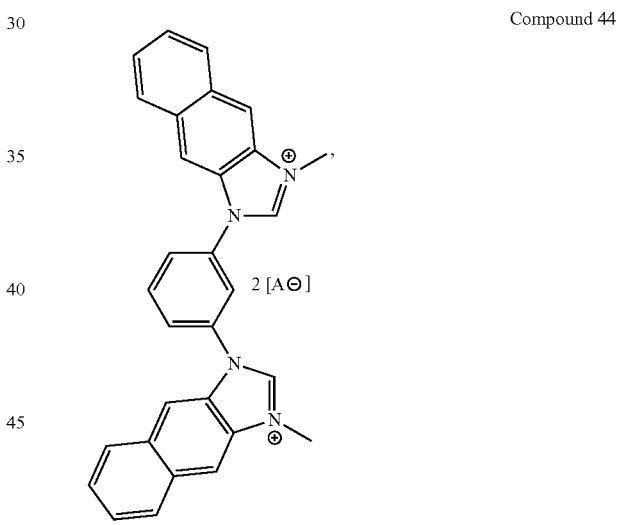
2 [A⊖]
Compound 45
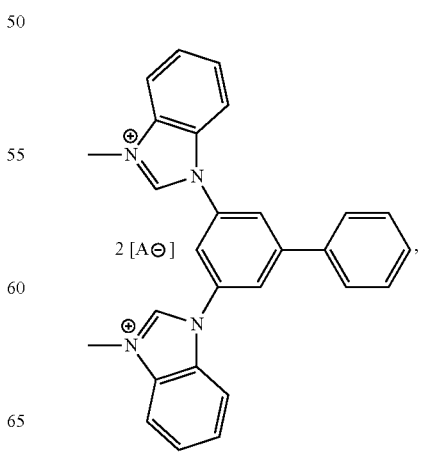
2 [A⊖]

-continued
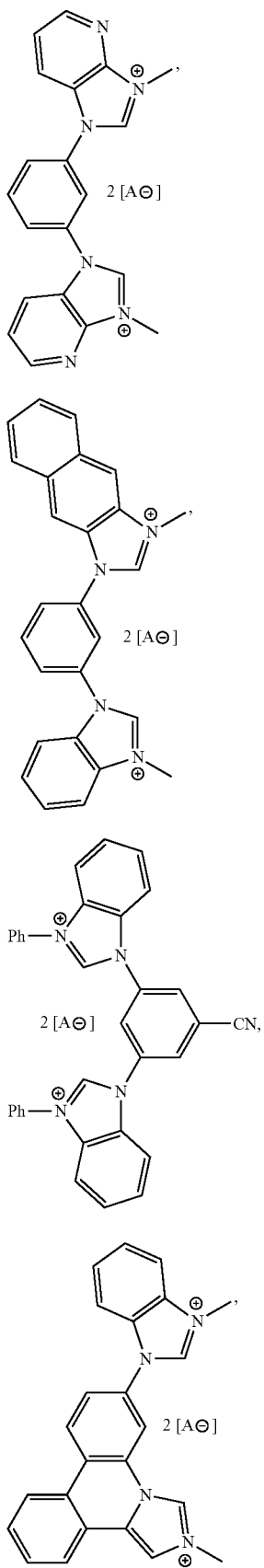
-continued
Compound 46
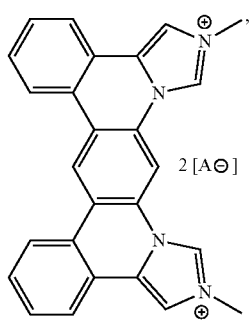
Compound 47
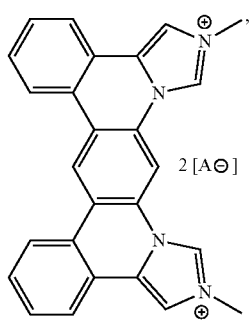
Compound 48
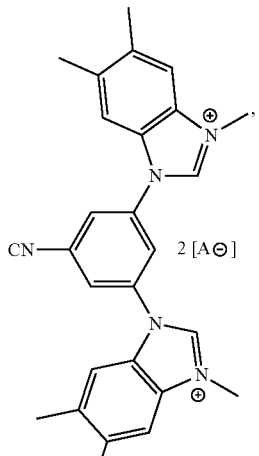
Compound 49
Compound 50
Compound 51
Compound 52
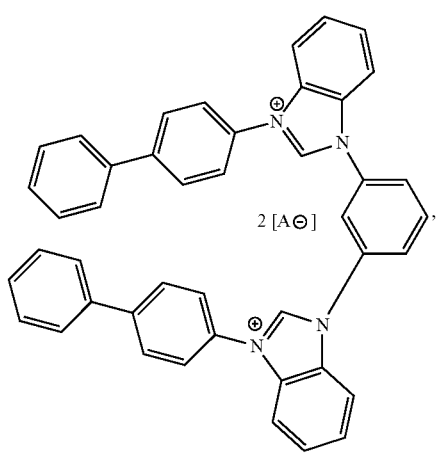
Compound 53
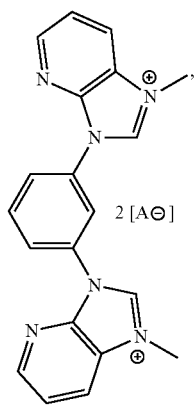

-continued
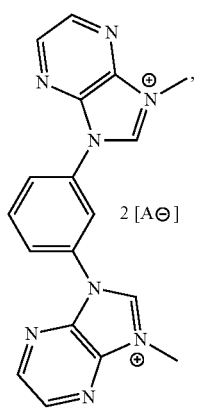
Compound 54
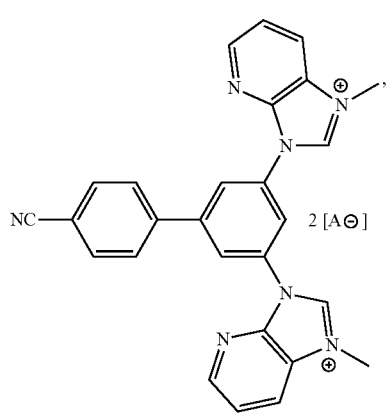
Compound 55
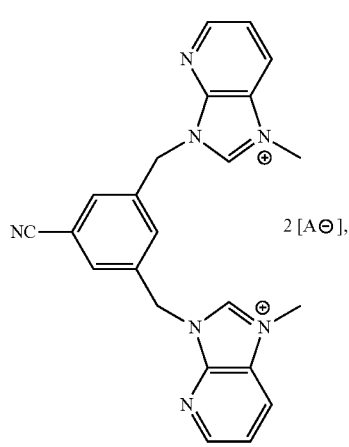
Compound 56
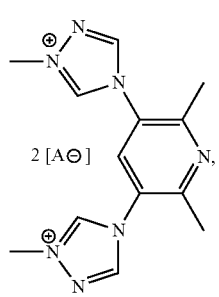
Compound 57
-continued
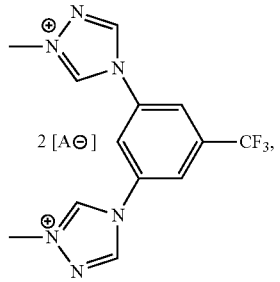
Compound 58
Compound 59
Compound 60

-continued
Compound 61
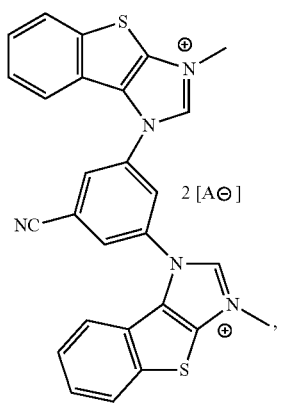
2 [A⊖]
Compound 62
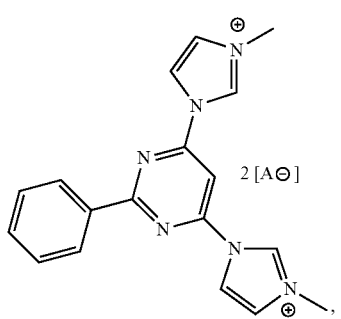
2 [A⊖]
Compound 63
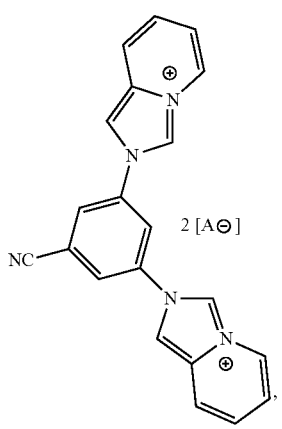
2 [A⊖]
Compound 64
2 [A⊖]
-continued
Compound 65
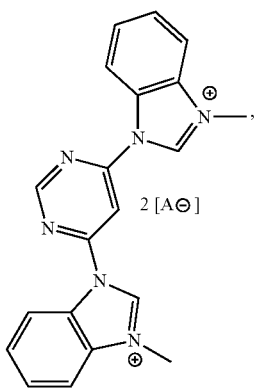
2 [A⊖]
Compound 66
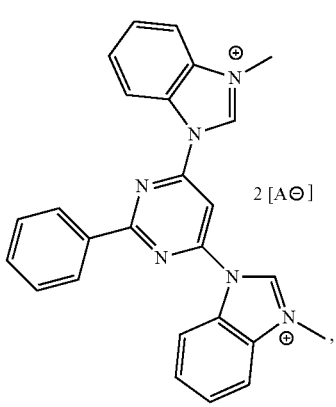
2 [A⊖]
Compound 67
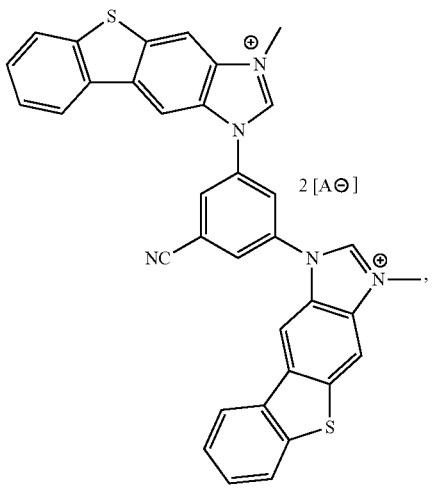
2 [A⊖]

125
-continued
Compound 68
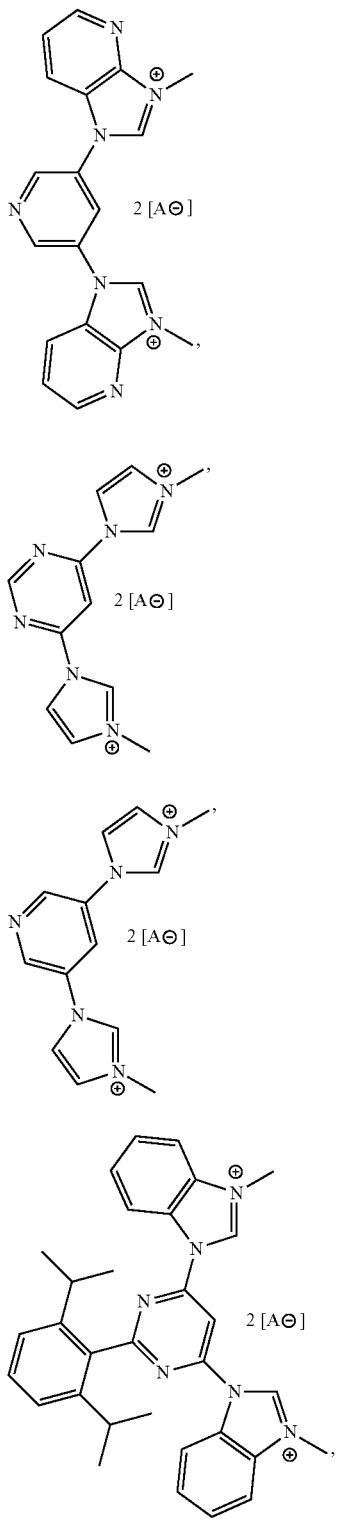
Compound 69
Compound 70
Compound 71
126
-continued
Compound 72
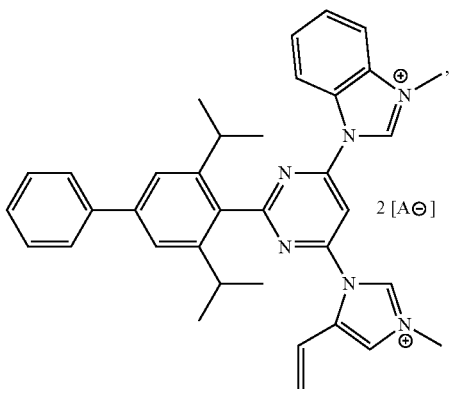
Compound 73
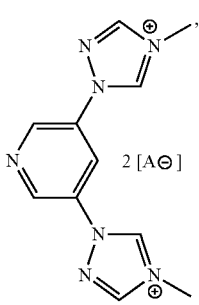
Compound 74
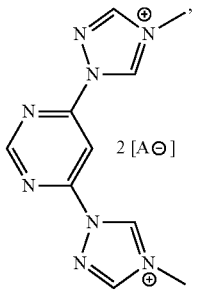
Compound 75
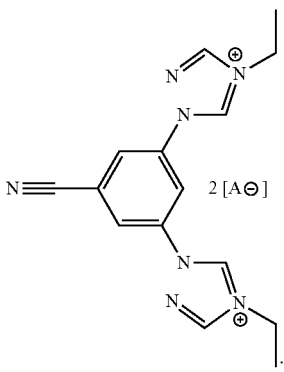
14. The method according to claim 1, wherein L is DMSO.
15. The method according to claim 1, wherein L is THF.
16. The method according to claim 1, wherein L is CH$_3$CN.
* * * * *